(12) United States Patent
Kaib et al.

(10) Patent No.: US 10,105,055 B2
(45) Date of Patent: *Oct. 23, 2018

(54) SYSTEMS AND METHODS FOR COMMUNICATING DATA

(71) Applicant: Zoll Medical Corporation, Chelmsford, MA (US)

(72) Inventors: Thomas E. Kaib, Irwin, PA (US); Shane Volpe, Saltsburg, PA (US); Marshal Linder, New Kensington, PA (US); Patrick Hresko, Mount Pleasant, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/805,703

(22) Filed: Nov. 7, 2017

(65) Prior Publication Data

US 2018/0125363 A1   May 10, 2018

Related U.S. Application Data

(63) Continuation of application No. 15/203,364, filed on Jul. 6, 2016, now Pat. No. 9,839,356.

(Continued)

(51) Int. Cl.
| | |
|---|---|
| G08C 19/22 | (2006.01) |
| A61B 5/00 | (2006.01) |
| A61B 5/0402 | (2006.01) |
| A61N 1/39 | (2006.01) |
| A61B 5/0404 | (2006.01) |
| A61N 1/04 | (2006.01) |
| A61N 1/362 | (2006.01) |
| G06F 19/00 | (2018.01) |
| G16H 40/67 | (2018.01) |
| A61B 5/021 | (2006.01) |
| A61B 5/024 | (2006.01) |

(Continued)

(52) U.S. Cl.
CPC ......... *A61B 5/0022* (2013.01); *A61B 5/0402* (2013.01); *A61B 5/0404* (2013.01); *A61B 5/6804* (2013.01); *A61N 1/046* (2013.01); *A61N 1/0484* (2013.01); *A61N 1/3625* (2013.01); *A61N 1/39* (2013.01); *A61N 1/3968* (2013.01); *G06F 19/00* (2013.01); *G16H 40/67* (2018.01); *A61B 5/021* (2013.01); *A61B 5/024* (2013.01); *A61B 5/1118* (2013.01); *A61N 1/37* (2013.01)

(58) Field of Classification Search
None
See application file for complete search history.

(56) References Cited

U.S. PATENT DOCUMENTS

| | | | |
|---|---|---|---|
| 4,928,690 | A | 5/1990 | Heilman et al. |
| 5,078,134 | A | 1/1992 | Heilman et al. |
| 5,741,306 | A | 4/1998 | Glegyak et al. |
| 5,944,669 | A | 8/1999 | Kaib |

(Continued)

*Primary Examiner* — Adolf Dsouza
(74) *Attorney, Agent, or Firm* — Zoll Medical Corporation

(57) ABSTRACT

An external medical device including monitoring circuitry and communication circuitry. The monitoring circuitry monitors a cardiac condition of a patient using the external medical device. For example, the communication circuitry initiates a communication link with a remote location. The remote location can be selected based on data associated with at least one of the external medical device and the patient using the external medical device. In some examples, supporting data can be transmitted to the remote location.

20 Claims, 9 Drawing Sheets

Related U.S. Application Data

(60) Provisional application No. 62/189,583, filed on Jul. 7, 2015.

(51) Int. Cl.
    *A61B 5/11*     (2006.01)
    *A61N 1/37*     (2006.01)

(56) References Cited

U.S. PATENT DOCUMENTS

| | | |
|---|---|---|
| 6,065,154 A | 5/2000 | Hulings et al. |
| 6,125,176 A | 9/2000 | Foladare et al. |
| 6,253,099 B1 | 6/2001 | Oskin et al. |
| 6,280,461 B1 | 8/2001 | Glegyak et al. |
| 6,603,847 B1 | 8/2003 | Griffith |
| 6,681,003 B2 | 1/2004 | Linder et al. |
| 6,970,737 B1 | 11/2005 | Brodnick et al. |
| 6,980,112 B2 | 12/2005 | Nee |
| 8,185,623 B2 | 5/2012 | Lewis et al. |
| 8,271,082 B2 | 9/2012 | Donnelly et al. |
| 8,369,944 B2 | 2/2013 | Macho et al. |
| 8,433,399 B1 | 4/2013 | Nosrati et al. |
| 8,565,871 B2 * | 10/2013 | Tuysserkani ......... A61B 5/0022 340/539.12 |
| 8,676,313 B2 | 3/2014 | Volpe et al. |
| 2004/0034284 A1 * | 2/2004 | Aversano ............. A61B 5/0006 600/300 |
| 2005/0282566 A1 | 12/2005 | Bixler et al. |
| 2006/0214786 A1 | 9/2006 | Bixler et al. |
| 2011/0178373 A1 | 7/2011 | Pacey et al. |
| 2015/0039039 A1 | 2/2015 | MacHo et al. |
| 2015/0039042 A1 | 2/2015 | Amsler et al. |

* cited by examiner

Please select a reason for initiating communications:

| Technical Question | Device Error Code | Health Issue |
| Training Request | Device Issue | Other |

SYSTEMS AND METHODS FOR COMMUNICATING DATA

CROSS REFERENCE TO RELATED APPLICATIONS

This application is a continuation of U.S. patent application Ser. No. 15/203,364 entitled "Systems and Methods for Communicating Data", filed Jul. 6, 2016 which claims the benefit of priority from U.S. Provisional Patent Application No. 62/189,583, entitled "Systems and Methods for Communicating Data" and filed Jul. 7, 2015, which are incorporated herein by reference in their entirety.

TECHNICAL FIELD

The present disclosure relates to an external medical device and, in some aspects, to an external medical device configured to communicate with a remote location.

BACKGROUND

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

Monitoring devices are also available. For example, such devices operate by monitoring the patient's heart for treatable arrhythmias and, when such is detected, the device applies corrective electrical pulses directly to the heart. Wearable pacing devices and/or defibrillators have been developed for a certain population of patients, e.g., those that may have recently experienced a heart attack, that are susceptible to heart arrhythmias and are at temporary risk of sudden death, or that are awaiting an implantable device.

Typically, these external monitoring and/or pacing devices and/or defibrillators include communication circuits capable of communicating with a remote location.

SUMMARY

Preferred and non-limiting aspects or embodiments of the present invention will now be described in the following numbered clauses:

Clause 1. A wearable medical device includes monitoring circuitry configured to monitor a cardiac condition of a patient using the wearable medical device; and communication circuitry configured to initiate an audio and/or video communication link with a remote location. The remote location is selected based on data associated with at least one of the wearable medical device and the patient using the wearable medical device.

Clause 2. The wearable medical device of clause 1, wherein the communication circuitry can initiate the audio and/or video communication link by placing a call, and the call can routed to the remote location based on the data associated with at least one of the wearable medical device and the patient using the wearable medical device.

Clause 3. The wearable medical device of any of clause 1 and 2, wherein the data can include data collected over a period of time during which the patient is using the wearable medical device.

Clause 4. The wearable medical device of any of clauses 1 to 3, wherein the data collected over the period of time can be continuously or substantially continuously collected during the period of time.

Clause 5. The wearable medical device of any of clauses 1 to 4, wherein the monitoring circuitry can be configured to monitor the cardiac condition of the patient during the period of time.

Clause 6. The wearable medical device of any of clauses 1 to 5, wherein the data can include compliance data of the patient.

Clause 7. The wearable medical device of any of clauses 1 to 6, wherein the data can include at least one of an indication of a compliance of the patient with a requirement for using the wearable medical device during a period of time, patient training data, and device event data.

Clause 8. The wearable medical device of any of clauses 1 to 7, wherein the data can include patient training data.

Clause 9. The wearable medical device of any of clauses 1 to 8, wherein the data can include device abuse information.

Clause 10. The wearable medical device of any of clauses 1 to 9, wherein the communication circuitry can be configured to automatically initiate the communication link on detecting at least one of a patient event and a device event.

Clause 11. The wearable medical device of any of clauses 1 to 10, wherein the data can be received from a remote data source.

Clause 12. The wearable medical device of any of clauses 1 to 11, wherein the communication circuitry can initiate the audio and/or video communication link with the remote location in response to a user instruction.

Clause 13. The wearable medical device of any of clauses 1 to 12, wherein the communication circuitry can automatically initiate the audio and/or video communication link with the remote location based on the data associated with at least one of the wearable medical device and the patient using the wearable medical device.

Clause 14. The wearable medical device of any of clauses 1 to 13, wherein the communication circuitry can automatically initiate a second communication link concurrently or substantially concurrently with the audio and/or video communication link with the remote location.

Clause 15. The wearable medical device of any of clauses 1 to 14, wherein the communication circuitry can automatically initiate the second communication link with a predetermined other remote location concurrently or substantially concurrently with the audio and/or video communication link with the remote location.

Clause 16. The wearable medical device of any of clauses 1 to 15, wherein the communications link can include a real-time call including voice and/or video communication between the communication circuitry and the remote location.

Clause 17. The wearable medical device of any of clauses 1 to 16, wherein the communication circuitry can be configured to receive a request for certain data from the remote location, and the communication circuitry can be configured to provide the certain data to the remote location in response to the request.

Clause 18. The wearable medical device of any of clauses 1 to 17, wherein the communication circuitry can be configured to provide to the remote location direct access to certain data stored in a memory of the wearable medical device.

Clause 19. The wearable medical device of any of clauses 1 to 18, wherein audio and/or video data can be communicated via the audio and/or video communication link, and the communication circuitry can be configured to transmit supporting data to the remote location.

Clause 20. The wearable medical device of any of clauses 1 to 19, wherein the wearable medical device can further include a garment worn by the patient, and the garment can include an electrode assembly including a plurality of electrodes. The plurality of electrodes can be configured to receive a plurality of different ECG signals from the patient, and the data can include the plurality of different ECG signals.

Clause 21. The wearable medical device of any of clauses 1 to 20, wherein the data comprises at least one of monitored physiological data, patient symptom data, location/position data, patient profile and preferences data, treatment data, and device parameter data. The monitored physiological data includes information relating to a monitored physiological condition of the patient including data indicating at least one of an activity level of the patient, monitored ECG data, heart sounds, lung sounds, monitored tissue and/or lung fluids, blood pressure, heart rate, glucose levels, blood oxygen levels, thoracic impedance, respiration rate, sleep data, acoustics, stress levels of the patient, and a change in a monitored physiological conditions. The patient symptom data includes data indicating at least one of shortness of breath, light headedness, racing heart, skipped beat, fatigue, fainting, and chest discomfort. The location/position data includes information relating a patient's location including at least one of GPS coordinates, address of location, location within a building or a home, position of the patient, and altitude from a reference level. The patient profile and preference data includes one or more patient profile and preferences information including at least one demographics information, a language preference of the patient, a reason for selecting the communication link, data indicating a representative who assigned the patient the wearable medical device, a primary care physician or other caregiver assigned to the patient, and insurance data. The treatment data includes information relating to a treatment event including data indicating at least one of a treatment for a detected cardiac event of the patient and treatment parameters. The device parameter data includes data indicating at least one of a battery level of a battery pack of the device, a unique device identifier, device type, device technical history, and technical data associated with a reported technical issue of the device.

Clause 22. The wearable medical device of any of clauses 1 to 21, wherein the remote location can be further selected based on data associated with a plurality of possible remote locations.

Clause 23. The wearable medical device of any of clauses 1 to 22, wherein the wearable medical device can further include a processor configured to apply a plurality of rules to the data associated with the plurality of possible remote locations and the data associated with at least one of the wearable medical device and the patient using the wearable medical device to select the remote location from the plurality of possible remote locations.

Clause 24. The wearable medical device of any of clauses 1 to 23, wherein the data associated with the plurality of possible remote locations can include at least one of a schedule of availability of the plurality of possible remote locations, a location of the plurality of possible remote locations, and a type of personnel assigned to the plurality of possible remote locations.

Clause 25. The wearable medical device of any of clauses 1 to 24, wherein the wearable medical device can include a wearable cardiac monitoring device.

Clause 26. The wearable medical device of any of clauses 1 to 25, wherein the wearable medical device can include a wearable cardiac monitoring and treatment device.

Clause 27. The wearable medical device of any of clauses 1 to 26, wherein the wearable medical device can include a wearable defibrillator.

Clause 28. The wearable medical device of any of clauses 1 to 27, wherein the wearable medical device can include a wearable pacing device.

Clause 29. A wearable medical device includes monitoring circuitry configured to monitor a cardiac condition of a patient using the wearable medical device; and communication circuitry configured to initiate an audio and/or video communication link with at least one of a first remote location for providing technical support for the wearable medical device and a second remote location associated with a caregiver of the patient. The at least one of the first remote location and the second remote location can be selected based on data associated with an operation of the wearable medical device.

Clause 30. The wearable medical device of clause 29, wherein the at least one of the first remote location and the second remote location can be further selected based on data associated with the first remote location and data associated with the second remote location.

Clause 31. The wearable medical device of any of clauses 29 and 30, wherein the data can include at least one of data associated with a medical event of the patient detected by the monitoring circuitry and data associated with a treatment attempted or applied by the wearable medical device.

Clause 32. The wearable medical device of any of clauses 29 to 31, wherein audio and/or video data can be communicated via the audio and/or video communication link, and the communication circuitry can be configured to transmit supporting data to the at least one of the first remote location and the second remote location.

Clause 33. The wearable medical device of any of clauses 29 to 32, wherein the communication circuitry can initiate the audio and/or video communication link by placing a call, and the call can be routed to a sub-location of the one of the first remote location and the second remote location based on the supporting data.

Clause 34. The wearable medical device of any of clauses 29 to 33, wherein the data can include technical information relating to the wearable medical device.

Clause 35. The wearable medical device of any of clauses 29 to 34, wherein the data can include technical information associated with one or more error codes displayed to the patient.

Clause 36. A wearable medical device includes monitoring circuitry operative for monitoring a cardiac condition of a patient using the wearable medical device; and communication circuitry operative for initiating an audio and/or video communication link with a remote location. The communication circuitry can be configured to transmit supporting data to the remote location and initiate the audio and/or video communication link.

Clause 37. The wearable medical device of clause 36, wherein the communication circuitry can be configured to transmit the supporting data to the remote location contemporaneously or substantially contemporaneously with initiating the audio and/or video communication link.

Clause 38. The wearable medical device of any of clauses 36 and 37, wherein the communication circuitry can be configured to provide a prompt to a user prior to transmitting the supporting data to the remote location.

Clause 39. The wearable medical device of any of clauses 36 to 38, wherein the communication circuitry is further configured to provide a prompt to a user at least one of prior to initiating the audio and/or video communication link and prior to transmitting data to the remote location over the audio and/or video communication link, and wherein the user prompt comprises a prompt for user consent to release information to the remote location.

Clause 40. The wearable medical device of any of clauses 36 to 39, wherein the communication circuitry can be configured to transmit the supporting data to the remote location after the initiation of the audio and/or video communication link.

Clause 41. The wearable medical device of any of clauses 36 to 40, wherein the supporting data can include data associated with at least one of the wearable medical device and the patient using the wearable medical device.

Clause 42. The wearable medical device of any of clauses 36 to 41, wherein the communication circuitry can initiate the audio and/or video communication link by placing a call, and the call can be routed to the remote location based on the supporting data.

Clause 43. The wearable medical device of any of clauses 36 to 42, wherein the communication circuitry can transmit the supporting data to the remote location via another communication link separate from the audio and/or video communication link.

Clause 44. The wearable medical device of any of clauses 36 to 43, wherein the supporting data can include data collected over a period of time during which the patient is using the wearable medical device.

Clause 45. A wearable medical device includes monitoring circuitry configured to monitor a cardiac condition of a patient using the wearable medical device; and communication circuitry configured to initiate an audio and/or video communication link with a remote location. The remote location can be selected based on a previous communication link initiated by the communication circuitry with a previous remote location.

Clause 46. The wearable medical device of clause 45, wherein the remote location can be selected based on a plurality of different previous communication links initiated by the communication circuitry with a plurality of different previous remote locations.

Clause 47. The wearable medical device of any of clauses 45 and 46, wherein the remote location can be selected based on data transmitted by the communication circuitry to the previous remote location.

Clause 48. The wearable medical device of any of clauses 45-47, wherein the remote location can be selected based on a particular technical support agent associated with the previous remote location.

Clause 49. The wearable medical device of any of clauses 45-48, wherein the remote location can selected based on data associated with at least one of the wearable medical device and the patient using the wearable medical device.

Clause 50. A wearable medical device includes monitoring circuitry configured to monitor a cardiac condition of a patient using the wearable medical device; and communication circuitry configured to transmit a message to a remote location. The remote location can be selected based on data associated with at least one of the wearable medical device and the patient using the wearable medical device.

Clause 51. The wearable medical device of clause 50, wherein the message can include a text message.

Clause 52. The wearable medical device of any of clauses 50 and 51, wherein the communication circuitry can be further configured to provide a prompt to the patient that requests the patient indicate a nature of a communication with the remote location.

Clause 53. The wearable medical device of any of clauses 50 to 52, wherein the prompt can include a user interface including a plurality of different options for indicating the nature of the communication.

Clause 54. The wearable medical device of any of clauses 50 to 53, wherein the remote location can be selected based on the nature of the communication.

Clause 55. The wearable medical device of any of clauses 50 to 54, wherein the communication circuitry can be configured to transmit the message to the remote location, and wherein the remote location is selected based on information included in the message.

Clause 56. The wearable medical device of any of clauses 50 to 55, wherein the communication circuitry can be configured to transmit the message to the remote location to trigger the remote location to at least one of transmit another message to the device and initiate a communication link with the patient based on the data associated with at least one of the wearable medical device and the patient using the wearable medical device.

Clause 57. The wearable medical device of any of clauses 50-56, wherein the communication circuitry can be configured to transmit the message to the remote location to trigger the remote location to transmit the message based on at least one of the following: a determination of patient non-compliance, a detected patient condition, a detected pattern of the patient performing an operation incorrectly, a detected abuse of the device, a detected performance issue of the device.

Clause 58. The wearable medical device of any of clauses 50 to 57, wherein the communication circuitry can be configured to receive another message from the remote location, wherein the another message includes a request that the patient indicate a nature of a communication with the remote location.

Clause 59. A wearable medical device including monitoring circuitry configured to monitor a cardiac condition of a patient using the wearable medical device; and communication circuitry configured to initiate a communications link, and communication circuitry configured to determine a category of data associated with a communication link from a set of data categories, select a remote location from a plurality of remote locations based on the determined category of the data, and initiate the communication link to the remote location based on the determined category of the data.

Clause 60. The wearable medical device of clause 59, wherein the plurality of remote locations comprise an emergency response location, a technician location, a physician location, and a relative or caregiver location.

Clause 61. The wearable medical device of clauses 59 and 60, wherein the communication circuitry is configured to determine the category of the data as one of monitored physiological data, patient symptom data, location/position data, patient profile and preferences data, treatment data, and device parameter data.

Clause 62. The wearable medical device of any of clauses 59 to 61, wherein if the determined category is patient symptom data, the communication circuitry is configured to provide the data to the technician location for reviewing or editing the data before providing the data to the physician location.

Clause 63. The wearable medical device of any of clauses 59 to 62, wherein if the determined category is device data, the communication circuitry is configured to provide the data to the technician location.

Clause 64. The wearable medical device of any of clauses 59 to 63, wherein if the determined category is treatment data, the communication circuitry is configured to provide the data to the relative or caregiver location.

Clause 65. The wearable medical device of any of clauses 59 to 64, wherein the communication circuitry is configured to at least one of provide the data to the selected remote location and initiate an audio and/or video communication link with the selected remote location.

Clause 66. The wearable medical device of any of clauses 59-65, wherein the communication circuitry is configured to determine the category of data associated with the communication link from the set of data categories based on user input to the device.

Clause 67. The wearable medical device of any of clauses 59-66, wherein the communication circuitry is configured to determine the category of data associated with the communication link from the set of data categories based on one or more characteristics of the data.

Clause 68. The wearable medical device of any of clauses 1-33, wherein the remote location is one of an emergency response location, a technician location, a physician location, and a relative or caregiver location.

Clause 69. The wearable medical device of any of clause 1-33 and 68, wherein the communication circuitry is configured to determine the category of the data as one of monitored physiological data, patient symptom data, location/position data, patient profile and preferences data, treatment data, and device parameter data and select one of the emergency response location, the technician location, the physician location, and the relative or caregiver location as the remote location based on the determined category of the data.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DETAILED DESCRIPTION

Figure 1:
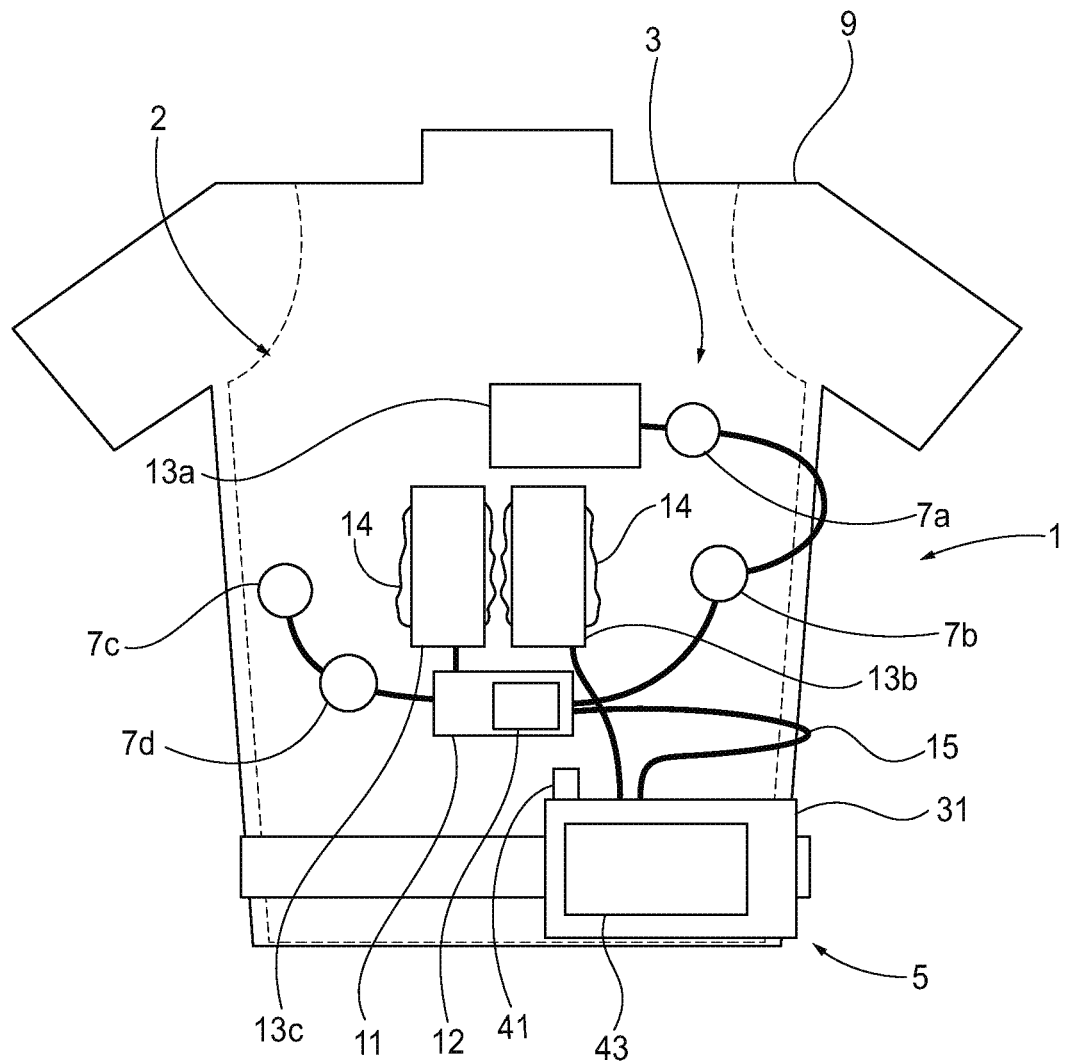
FIG. 1 is a schematic drawing of a wearable medical device.

As used herein, the singular form of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Unless indicated to the contrary, the numerical parameters set forth in the following specification and attached claims are approximations that can vary depending upon the desired properties sought to be obtained by the present disclosure.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

This disclosure relates to communication components, modules, subsystems, circuitry and/or techniques for use in external medical devices. For example, such communication components, modules, subsystems, circuitry and/or techniques can be used in the context of medical devices for monitoring and/or providing treatment to a patient. For example, such medical devices can include monitoring devices configured to monitor a patient for certain conditions. In some implementations, such devices are capable of, in addition to monitoring for patient conditions, providing treatment to a patient based on detecting a predetermined patient condition.

For example, external medical devices as disclosed herein can include cardiac monitoring and/or automated pacing devices or defibrillators, such as, in-facility monitoring defibrillators (e.g., for patients that are confined to a limited space within a facility, such as, within a hospital environment, to a patient's room) or outpatient wearable defibrillators or monitors. Such devices can be configured to monitor a patient for an arrhythmia condition such as bradycardia, ventricular tachycardia (VT) or ventricular fibrillation (VF). In addition, while the detection methods and systems described hereinafter are disclosed as detecting VT and VF, this is not to be construed as limiting the invention as other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventrical arrhythmias such as premature ventricular contractions (PVCs) and accelerated idioventricular rhythm, may also be detected. In the case of treatment devices, such as, pacing and/or defibrillating devices, if an arrhythmia condition is detected, the device can automatically provide a pacing or defibrillation pulse or shock to treat the condition.

External medical devices as disclosed herein can include wearable cardiac monitors and/or defibrillators (which can include pacing functionality). Devices described herein as external or non-invasive can be contrasted with invasive medical devices, such as implantable defibrillators or implantable pacing devices.

The external medical devices as described herein can include monitoring circuitry and communication circuitry. The monitoring circuitry can monitor a patient condition including one or more medical conditions. For example, the monitoring circuitry can, in addition to monitoring for cardiac conditions as described above, monitor for other physiological information or parameters, such as, without limitation, blood pressure, temperature, blood glucose levels, and blood oxygen levels. In one or more implementations, monitored physiological information or parameters can also include, without limitation, patient symptom data (e.g., patient-reported symptoms and/or automatically detected patient information), related cardiac data including premature ventricular contraction (PVC) count, heart rate information, heart sounds data, ECG data (e.g., continuous ECG data), lung fluid measurements/data, patient thoracic impedance measurements/data, and pectoral impedance measurements/data, and changes in such data. For example, the ECG data can be associated with the patient symptom data. For example, up to a one minute or more ECG recording can be associated with one or more patient-reported symptoms as described in further detail below. For example, the physiological data may be pre-tagged by the user (e.g., the patient) prior to transmission. In an example, the patient can input one or more annotations relating to the physiological information that is then transmitted along with the physiological information.

In various implementations, the external medical devices as described herein can be ambulatory, e.g., the device is capable of and designed for moving with the patient. For example, as described in detail below, the external medical device can be a wearable medical device. In some implementations, the external medical devices as described herein may be a portable medical device. For example, the device may be capable of being moved from one location to another by, e.g., a user such as an emergency responder or a caregiver.

The devices as described herein may be capable of continuously, substantially continuously, long-term and/or extended use or wear by, or attachment or connection to a patient.

For example, devices as described herein may be capable of being used or worn by, or attached or connected to a patient, without substantial interruption for a predetermined period of time. In some examples, such devices may be capable of being used or worn by, or attached or connected to a patient for example, up to hours or beyond (e.g., weeks, months, or even years).

In some implementations, such devices may be removed for a period of time before use, wear, attachment, or connection to the patient is resumed, e.g., to change batteries, to change the garment, and/or to take a shower, without departing from the scope of the examples described herein.

The devices as described herein may be capable of continuously, substantially continuously, long-term and/or extended monitoring of a patient.

For example, devices as described herein may be capable of providing cardiac monitoring without substantial interruption for a predetermined period of time. In some examples, such devices may be capable of continuously or substantially continuously monitoring a patient for cardiac-related information (e.g., ECG information, including arrhythmia information, heart sounds, etc.) and/or non-cardiac information (e.g., blood oxygen, the patient's temperature, glucose levels, and/or lung sounds), for example, up to hours or beyond (e.g., weeks, months, or even years).

In some implementations, such devices may be powered down for a period of time before monitoring is resumed, e.g., to change batteries, to change the garment, and/or to take a shower, without departing from the scope of the examples described herein.

In some instances, the devices may carry out its monitoring in periodic or aperiodic time intervals or times. For example, the monitoring during intervals or times can be triggered by a user action or another event. For example, one or more durations between the periodic or aperiodic intervals or times can be user-configurable.

In various implementations, the devices may be operated on battery power for a duration of the device's use after which the batteries may be replaced and/or recharged.

In accordance with an implementation, a medical device can include communication circuitry that can initiate an interactive communication link, including one or more of an audio and/or video communication link, a text messaging link, such as SMS message or MMS messaging, a real-time chat service, or other live support communication link, with a remote location. For example, the remote location can be selected based on data associated with at least one of the medical device and the patient using the medical device.

In some examples, the communication circuitry can be configured to initiate the interactive communication link with at least one of a first remote location for providing technical support for the medical device and a second remote location associated with a caregiver of the patient. As noted above, the communication link can be an audio and/or video communication link. Further, in some examples, the at least one of the first remote location and the second remote location can be selected based on data associated with an operation of the medical device. For example, one or more remote locations or destinations as described herein may include computer systems, devices (e.g., desktop computers, handheld devices, smartphones, or tablet computing devices), networks, telephone circuitry and equipment, and/or other communications systems to facilitate the receiving and sending of information as well as the establishment of communication links (such as video/audio and/or textual communication links) between the medical device 100 and the one or more remote locations. In some implementations, the one or more remote locations can include circuitry and/or equipment for recording the information transferred over the communication links. For example, audio/video calls and/or textual messages can be recorded and stored for later review. For example, audio/video conversations may be transcribed into a text transcript, including images, prior to being stored.

In an example, the communication circuitry can be operative for initiating an audio and/or video communication link with a remote location and configured to also transmit supporting data to the remote location via the audio and/or video communication link or a different communication channel. For example, the supporting data can be transmitted prior to, during or substantially during, or subsequent to initiating and maintaining the communication link.

In another example, the communication circuitry can be configured to initiate a communication link with a remote location, which is selected based on one or more previous communication links initiated by the communication circuitry with one or more prior remote locations. In this manner, the device may consider a history of prior communication links established with a plurality of remote locations in determining an appropriate location with which to establish a link.

Figure 4:
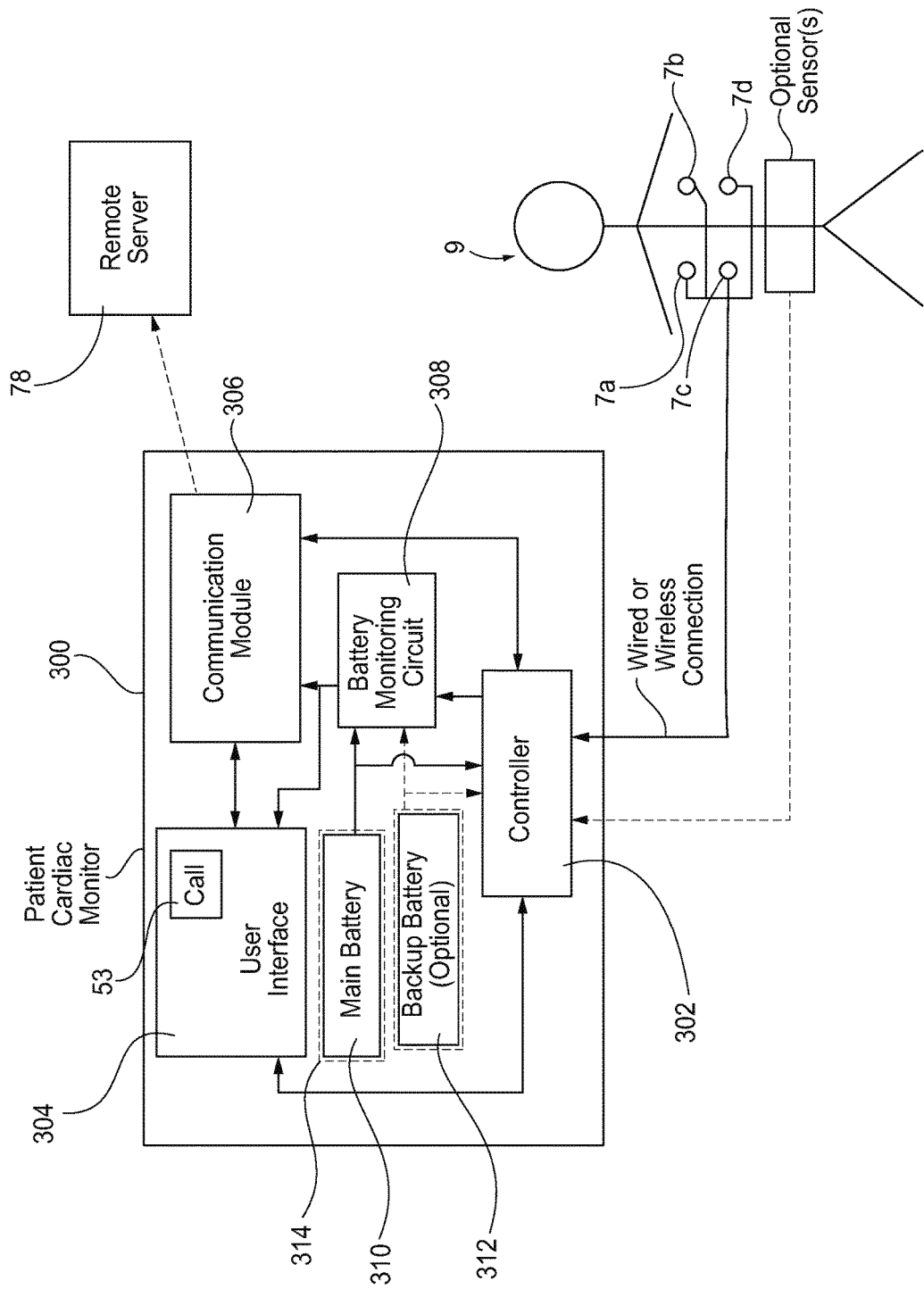
FIG. 4 is an example block diagram illustrating functional components of a patient monitor (e.g., a cardiac monitor)

In an example and with reference to FIGS. 1 and 4, an external medical device 100 can be configured as a wearable defibrillator 1, such as the LifeVest® wearable defibrillator available from ZOLL® Medical Corporation of Pittsburgh, Pa. and Chelmsford, Mass. The wearable defibrillator 1 can be worn by a patient 9 and can include a garment 2 (shown in phantom in FIG. 1), an electrode assembly 3, and a monitor 5 operatively connected to the electrode assembly 3.

The garment 2 can be configured as a harness, shirt, or other apparel and is configured to permit the defibrillator 1 to be worn by on about the torso of the patient 9. The electrode assembly 3 can be configured to be assembled within the garment 2.

Such wearable defibrillators may be configured for long term or extended wear. For example, the wearable defibrillator may be continuously or substantially continuously worn by a patient for two to three months at a time. During the period of time in which they are worn by the patient, the wearable defibrillator 1 can be configured to continuously or substantially continuously monitor the vital signs of the patient, to be user-friendly and accessible, to be as lightweight, comfortable, and portable as possible, and to be capable of delivering one or more life-saving therapeutic shocks when needed. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944; the entirety of all of which are incorporated by reference herein.

With continued reference to FIG. 1, the electrode assembly 3 includes a plurality of electrodes, such as electrodes 7a, 7b, 7c, and 7d, which contact a patient 9 when the wearable defibrillator 1 is worn by the patient 9. According to one example, the electrodes 7a, 7b, 7c, and 7d are configured to receive electrocardiograph (ECG) signals from the patient 9. For instance, the electrodes 7a, 7b, 7c, and 7d can be positioned on the patient 9 to receive ECG signals from a front-to-back channel and from a side-to-side channel. For example, the front-to-back (FB) channel can include one or more of electrodes 7a, 7b, 7c, and 7d positioned on the chest of the patient 9 and another one or more of the electrodes 7a, 7b, 7c, and 7d positioned on the back of the patient 9. For example, the side-to-side (SS) channel includes one of the electrodes 7a, 7b, 7c, and 7d positioned on the left side of the chest and another one of the electrodes 7a, 7b, 7c, and 7d positioned on the right side of the chest of the patient 9. In some examples, the electrodes 7a, 7b, 7c, and 7d can be operatively connected to a distribution node 11 of the electrode assembly 3.

In some implementations, the electrode assembly 3 can also comprise therapy pads 13a, 13b, and 13c operatively connected to the distribution node 11. The therapy pads 13a, 13b, and 13c can be configured to deliver one or more life-saving therapeutic shocks when needed. In some examples, the electrode assembly 3 can also include other sensing electrodes and devices (not shown) such as, but not limited to, heart beat sensors, accelerometers, and sensors capable of measuring blood pressure, heart rate, thoracic impedance, respiration rate, heart sounds, acoustic sensors, audio transducers, and the activity level of the subject. The electrode assembly 3 can further comprise a tactile stimulator 12, such as a vibrator, positioned within the distribution node 11 to provide tactile stimulation to the patient 9 as described in greater detail hereinafter.

The monitor 5 can be operatively connected to one or more of the therapy pads 13a, 13b, and 13c and electrodes 7a, 7b, 7c, and 7d via a trunk cable 15 or any other suitable cable or connection device. Wiring or other connection devices can be used to connect at least one portion of the distribution node 11 to the electrodes 7a, 7b, 7c, and 7d and therapy pads 13a, 13b, and 13c. Alternatively, the monitor 5 can be operatively connected to one or more of the electrodes 7a, 7b, 7c, and 7d, therapy pads 13a, 13b, and 13c, and distribution node 11 by a wireless connection or a combination of wireless and wired connections.

The distribution node 11 is configured to obtain ECG data from the electrodes 7a, 7b, 7c, and 7d, digitize this data, and transfer this data to the monitor 5. Accordingly, the distribution node 11 includes a processor, such as a belt node processor (BNP) 17 (see FIGS. 3, 4A, and 4B), operatively connected to electrodes 7a, 7b, 7c, and 7d and configured to receive signals representing the ECG of the patient 9 from the electrodes 7a, 7b, 7c, and 7d. The BNP 17 communicates with the monitor 5 via a Controller Area Network (CAN) bus 19 (see FIGS. 3, 4A, and 4B) or any other suitable bus that comprises trunk cable 15. The BNP 17 is also configured to sense whether one or more of electrodes 7a, 7b, 7c, and 7d have fallen off the patient's body, to control the tactile stimulator 12, and to fire the electrode gel interface for providing electrolytic gel 14 (FIG. 1) to the therapy pads 13a, 13b, and 13c when a request is received from the monitor 5.

Figure 2:
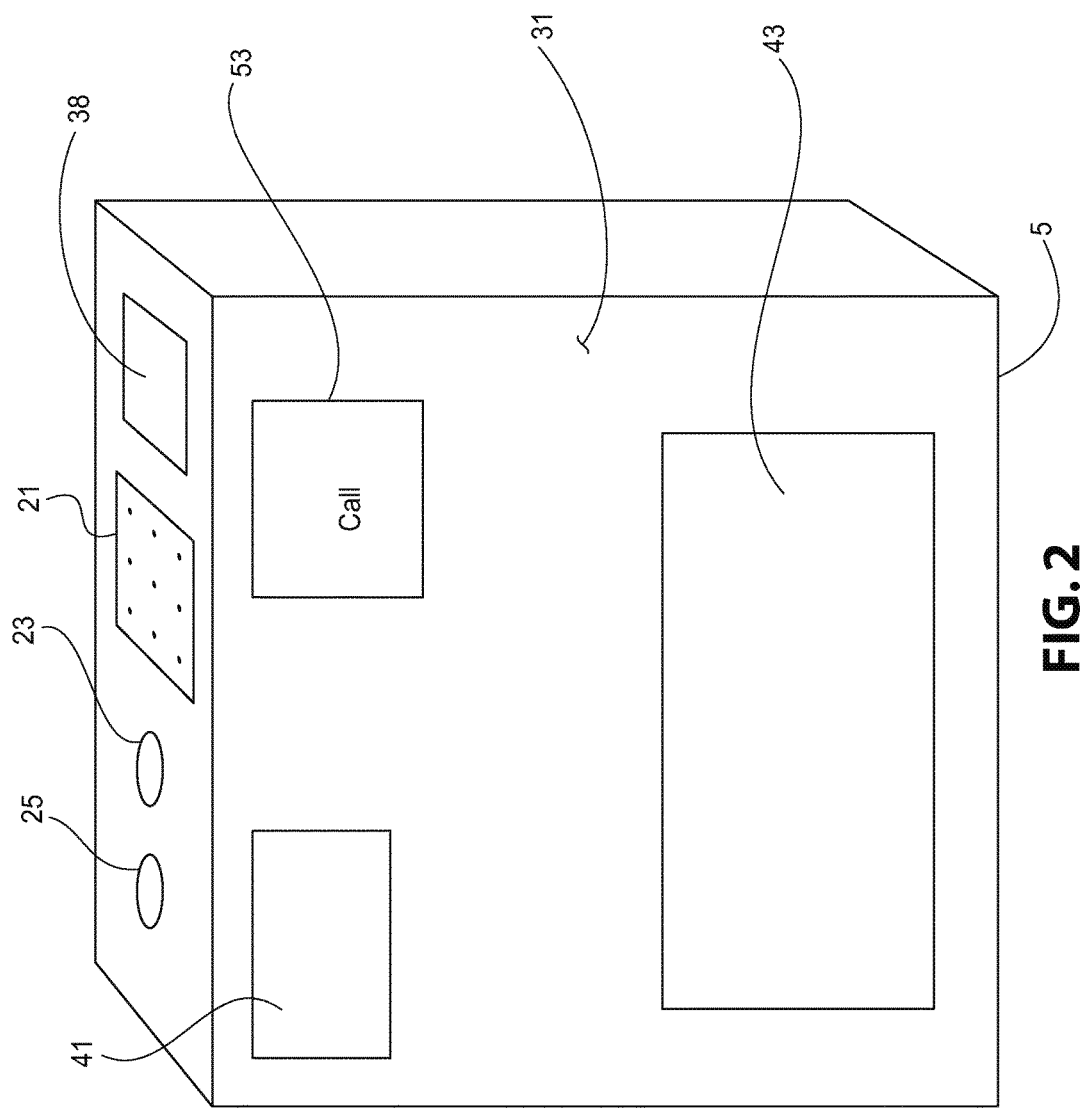
FIG. 2 is a block diagram of an example monitor for a wearable medical device.

With reference to FIG. 2, and with continuing reference to FIG. 1, the monitor 5 can include an external housing 31 having a port 38 to which the ECG electrodes 7a, 7b, 7c, and 7d and therapy pads 13a, 13b, and 13c of the electrode assembly 3 are operatively coupled to the monitor 5 via the trunk cable 15. The external housing 31 further comprises at least one, and for example, a pair of patient response buttons 41 positioned, for example, in the top left corner of the housing 31. The external housing 31 of the monitor 5 can also include a display screen 43 for providing information to the patient 9 and for providing a user input device to the patient 9. In other embodiments, visual indicators 25, such as LED bulbs, can be positioned on the housing 31 for providing information to the patient 9. The external housing 31 can include an audio system having a speaker 21 and a microphone 23 positioned on the external housing 31. The speaker 21 is desirably positioned at least 2.5 inches away from the microphone 23 to minimize feedback. As will be discussed herein, the display screen 43, visual indicators 25, and speaker 21 can be used for providing feedback and/or alerts to the patient 9.

Further details of the monitor 5 can be found in U.S. patent application Ser. No. 14/448,997, which is hereby incorporated by reference in its entirety.

In some implementations, the medical device as described herein can be a hospital-based wearable defibrillator and/or pacing device. For example, such a hospital-based device can include a defibrillator and/or pacing device configured for continuous or substantially continuous use, wear, connection, attachment, or monitoring to/of a patient in a hospital environment. The hospital-based device can include a plurality of therapy and sensing electrodes that are attached to the patient's skin. In some examples, the electrodes are disposable adhesive electrodes. In some implementations, the electrodes are affixed to an electrode assembly (a patch), which can then be adhesively attached to the patient's skin. The electrodes can be attached to the patient's skin at particular locations as prescribed by a trained professional.

In operation, the hospital-based device can include a monitor configured to operate in a manner that is different from that of the monitor of wearable defibrillator 1 described above with respect to FIG. 1. As described in more detail herein, an interface, prompts, and communication performed by the hospital-based device can be configured for and/or directed to a user other than the patient 9, e.g., a caregiver such as a nurse or a patient service representative. For example, a caregiver can program the device and/or set the device up for use by the patient 9. The interface, prompts, and communication can be directed to the patient 9 in scenarios such as when a response is required to let the device know whether or not the patient 9 is conscious, which can be used in deciding when to shock the patient 9, and when a patient is given an alert to call the caregiver.

In some implementations, the medical device as described herein can be a short-term medical device. For example, such a short-term medical device can include a defibrillator and/or pacing device configured for continuous or substantially continuous use, wear, connection, attachment, or monitoring to/of a patient for a shorter period of time than a long term wearable defibrillator (e.g., up to days, weeks, or months as deemed medically necessary). For example, such a short-term defibrillator can be configured to monitor a patient presenting with syncope (e.g., by analyzing the patient's cardiac activity for aberrant patterns that can indicate abnormal physiological function). In some examples, aberrant patterns may occur prior to, during, or after the onset of syncope symptoms. For example, the short-term outpatient defibrillator can include a plurality of electrodes and/or an electrode assembly (patch) that can be adhesively attached to the patient's skin. The patient may replace the electrodes and/or patches as prescribed. The electrodes can be positioned in a configuration similar to that of the hospital-based device described above.

As noted above, a wearable medical device can be used for a wide range of patient conditions or situations, including following a recent myocardial infarction or coronary revascularization. In some examples, the wearable medical device can give caregivers time to optimize medical therapy and assess a patient's long-term risk for sudden death. In some examples, the wearable medical device is configured to continuously monitor the patient's heart and, if a life-threatening heart rhythm is detected, the device can issue an alert to the patient. For example, the wearable medical device can include a user interface for interacting with the wearable medical device. The wearable medical device can also include one or more input mechanisms (e.g., buttons, soft keys, etc.) that the patient can interact with in order to respond to a treatment alert. In some examples, the wearable medical device issues a treatment alert before providing a treatment shock, and if the patient does not respond to the treatment alert (e.g., by touching, pressing or holding down one or more response buttons, soft keys, etc.), the wearable medical device can deliver the treatment shock to restore normal heart rhythm.

Figure 3:
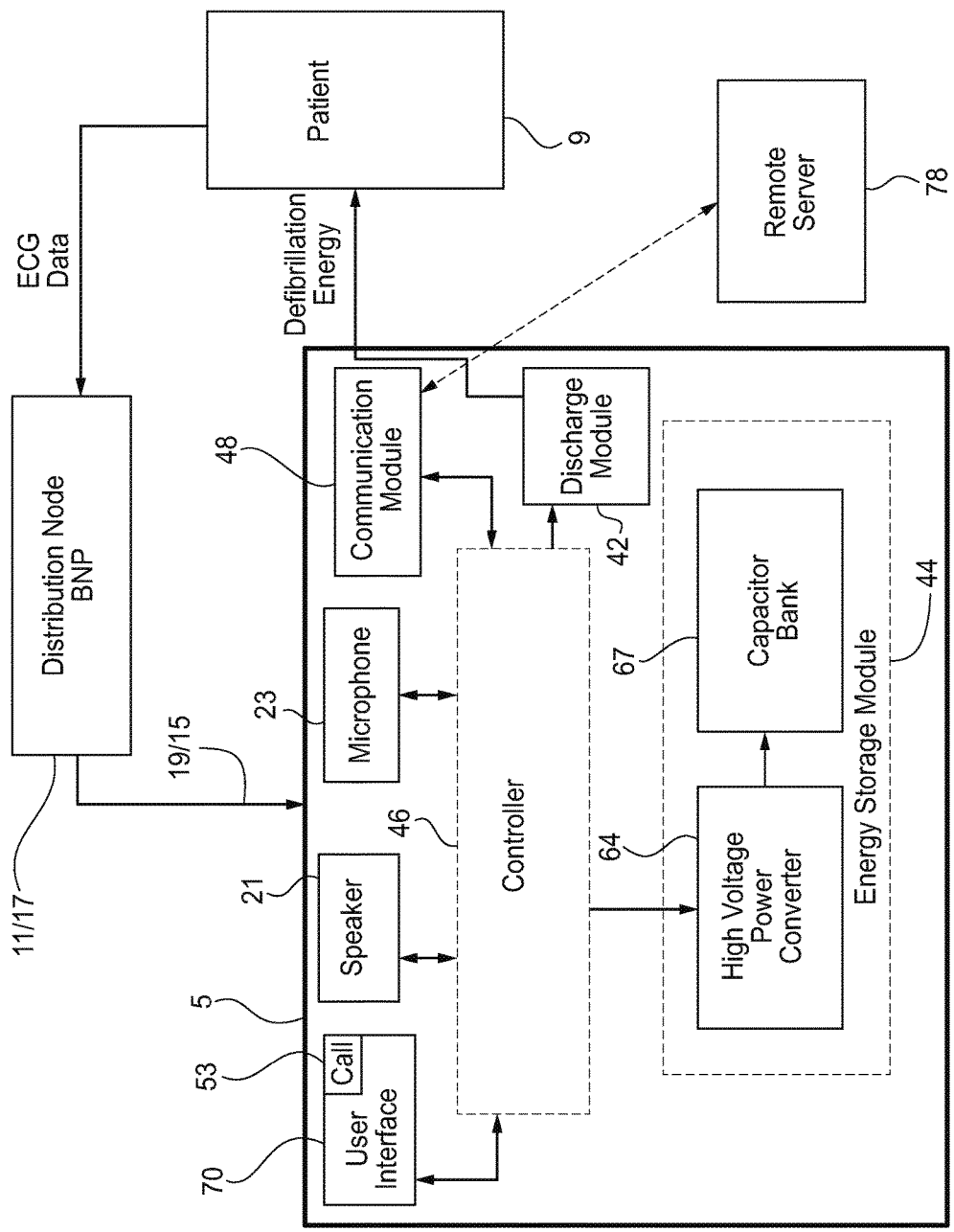
FIG. 3 is an example schematic diagram of a wearable medical device.

With reference to FIG. 3 and with continuing reference to FIGS. 1 and 2, the functional components of the monitor 5 can be provided within the external housing 31 of the monitor 5. In one example, the functional components of monitor 5 can be provided on a distributed printed circuit board as disclosed in U.S. patent application Ser. No. 14/448,857, which is hereby incorporated by reference in its entirety. In one example, the functional components of monitor 5 can comprise a discharge module 42, an energy storage module 44, a controller 46, and a communication module 48. The discharge module 42 is for selectively delivering an energy pulse to the patient 9 via therapy electrodes 13a, 13b, and 13c. The energy storage module 44 can be operatively connected to the discharge module 42. The controller 46 can be operatively connected to the energy storage module 44 and can be configured to control the delivery of the energy pulse to the patient 9. The communication module 48 can be operatively connected to the controller 46.

In one example, the energy storage module 44 can include a high voltage power convertor 64 (shown in FIG. 3) and a capacitive device, such as a bank of capacitors 67 (shown in FIG. 3). The monitor can comprise a battery pack (not shown), which provides power to the monitor 5 and/or wearable defibrillator 1. The discharge module 42 can include at least one high-voltage switch and can be configured to selectively deliver an energy pulse stored in the energy storage module 44 to the patient 9 based on a signal from the controller 46. The energy pulse is sent from the discharge module 42 through the port 38 to the patient 9 via therapy pads 13a, 13b, and 13c.

A biphasic waveform can be delivered to the patient 9 by switching the at least one high voltage switch of the discharge module 42. The operation of the pulse delivery system can be dynamic and depend on the patient's body impedance while the pulse is being delivered. For example, an amount of energy delivered can be held constant while varying the duration of the first phase and the second phase. In another example, a monophasic waveform can be delivered to the patient depending on the patient's condition or a condition of energy storage module 44.

With reference to FIG. 3, and with continuing reference to FIGS. 1 and 2, controller 46 can include one or more processors, each of which operates under the control of a control program that executes at runtime for performing certain functions of the medical device, e.g., wearable defibrillator 1.

Also or alternatively to the one or more processors, controller 46 can include discrete and/or integrated electrical and/or electronic circuitry that is configured to perform the functions described herein (either alone or in combination with one or more of processors), with or without a control program. In an example, the electrical and/or electronic circuitry of controller 46 can include one or more discrete elements, such as, without limitation, one or more of the following discrete elements: transistor, resistor, capacitor, inductor, memristor, diode, loudspeaker, buzzer, linear variable differential transformer (LVDT), rotary encoder, shaft encoder, inclinometer, motion sensor, vibration sensor, flow meter, strain gauge, accelerometer, thermocouple, thermopile, thermistor, resistance temperature detector (RTD), bolometer, thermal cutoff, magnetometer, gauss meter, hygrometer, photo resistor, LED or other light emitting device, and/or antenna.

In another example, the electrical and/or electronic circuitry of controller 46 can also or alternatively include one or more integrated circuits, such as, without limitation, analog integrated circuit, digital integrated circuit, mixed signal (analog and digital) integrated circuit, application specific integrated circuit (ASIC), programmable logic device (PLD), gate array, field programmable gate array (FPGA), and/or microelectromechanical systems (MEMS). In an example, these one or more integrated circuits can include one or more of analog-to-digital converter (ADC), a multiplexer, a power regulator, or some combination thereof.

In another example, controller 46 is operatively connected to a user interface 70 (comprised of one or more response buttons 41 and/or display screen 43), the high voltage power convertor 64, and the discharge module 42. Such configuration allows controller 46 to provide output to a patient 9, for example through the display screen 43 and/or speaker 21, and accept input from the patient 9, for example from response buttons 41 and/or display screen 43 when configured as a touch screen, as well as provide instructions to the high voltage power converter 64 and/or the discharge module 42 to deliver a therapeutic shock to the patient 9. For example, controller 46 can be used to provide certain functions within the wearable defibrillator 1 such as, but not limited to: high voltage converter control; discharge module control; real time clock (RTC) 34 (Date/time) for the system; execution of timing-critical software or functions such as therapy pulse synchronization (e.g., synchronizing the pulse delivery to avoid delivering a pulse on a T wave); ECG acquisition from the CAN bus 19; ECG monitoring and arrhythmia detection; user interface control; treatment sequencing; audio message generation; and data communications and storage. An example of the methods used to detect abnormal heart rhythms can be found in U.S. Pat. No. 5,944,669, which is assigned to the assignee of the present application and which is hereby incorporated by reference in its entirety.

In some implementations, the BNP 17 can be operatively connected to the controller 46. The BNP 17 can act as an ECG data acquisition engine for the controller 46 via the CAN bus 19 as described hereinabove.

In an example, the communication module 48 can be controlled by controller 46 and can provide one or more communication devices for communicating information to and from the monitor 5. For example, the communication module 48 can include one or more communication devices, such as, without limitation, a GPS transceiver, a Bluetooth transceiver, a Wi-Fi modem, and/or a cellular modem. The communication module 48 is configured to communicate with a remote server 78 and/or other remote locations via one or more communication devices, e.g., the cellular modem. The communication module 48 can also communicate with the remote server 78 and/or the other remote locations via another communication device, e.g., the Wi-Fi modem. For example, if the communication capabilities of one of the communication devices is not available (e.g., the cellular communications capabilities), the communications module 48 can communicate with the remote server 78 via one of the other communication devices.

In an example, the user interface 70 can provide one or more "call" buttons 53 (or one or more of the response buttons 41 can be configured as a "call" button) that accept input from a user (e.g., the patient 9) when the user actuates the call button 53. For example, the communications module 48 can be controlled by the controller 46 to initiate an audio and/or video communication link with a remote location in response to actuation of the "call" button 53. In an implementation, the display screen 43 can display the "call" button 53 as an icon selectable by the patient 9 via the user interface provided by the display screen 43 and which controls the communications module 48 to call the remote location. In some examples, the user can initiate the communication link through other techniques known in the art. For instance, the user may initiate the communication link by speak a voice command, e.g., "Call Service," or "Call Operator."

For the purpose of simplicity, references hereinafter will be made to monitor 5 shown in FIGS. 1, 3A and 4 that includes controller 46. However, this is not to be construed as limiting the invention since it is envisioned that controller 46 can include any suitable and/or desirably combination processor(s) and/or circuitry.

It should be appreciated that in various implementations, the communication link(s) described herein can be initiated and/or maintained without materially affecting other functions of the medical device, including, the monitoring, alerting, and/or treating aspects of the device.

In another example and with reference to FIG. 4, it is envisioned that the external medical device 100 as described herein can include a mobile patient monitor, for example, a cardiac monitor. As such, communications described herein can also be used in connection with the patient monitor 300.

The monitor 300 can include a controller 302 that is communicatively coupled (e.g., wired or wirelessly coupled) to receive from sensors and/or electrodes 7a-7d appropriately positioned on patient 9 signals (e.g., ECG data and/or heart sounds data from an acoustic sensor) indicative of cardiac activity of patient 9. In some examples, the sensors and/or electrodes can be an integral part of the housing structure of the patient monitor.

In some examples, the patient monitor 300 can be a cardiac monitor configured to receive cardiac data (e.g., ECG data and/or heart sounds data from an acoustic sensor). In some examples, the patient monitor 300 can, in addition to cardiac monitoring, perform monitoring of other relevant patient physiological information and/or parameters, e.g., glucose levels, blood oxygen levels, lung fluids, lung sounds, and blood pressure. In some examples, the patient monitor 300 can include motion sensors to track patient movement. For example, the patient monitor 300 can be in the form of an application on a handheld device, such as, a smartphone, a personal digital assistant, or a tablet device. In such implementations, the communication techniques described herein can be used in connection with monitoring the battery life status of the battery of the smartphone, personal digital assistant, or tablet device.

As shown, the patient monitor 300 can communicate with a remote server 78 or other remote location (e.g., one or more computer systems). For example, the patient monitor 300 may communicate with another device, which may be a remote handheld device (e.g., a smartphone, a personal digital assistant, or a tablet device). For example, the patient monitor 300 may periodically (e.g., on a preset schedule) and/or aperiodically (e.g., when prompted by an operator) establish a wireless communication (e.g., cellular communication, Wi-Fi or Bluetooth) to transfer patient data to the remote server 78.

In an example, patient monitor 300 can include a user interface 304, a communications module 306 and a battery monitoring circuit 308 coupled to controller 302. A main battery 310 and an optional backup battery 312 can be used to supply electrical power for the operation of controller 302, user interface 304, communications module 306 and battery monitoring circuit 308. Main battery 310 can be a rechargeable battery that is received in a battery receptacle 314 of patient monitor 300. Optional backup battery 312 can be a rechargeable battery or a single use battery.

In an example, the communication module 306 includes similar communication devices and operates in a similar manner as described above in connection with communication module 48. For example, the user interface 304 can provide one or more "call" buttons 53 that accept input from a user (e.g., the patient 9) when the user actuates the call button 53.

Figure 5:
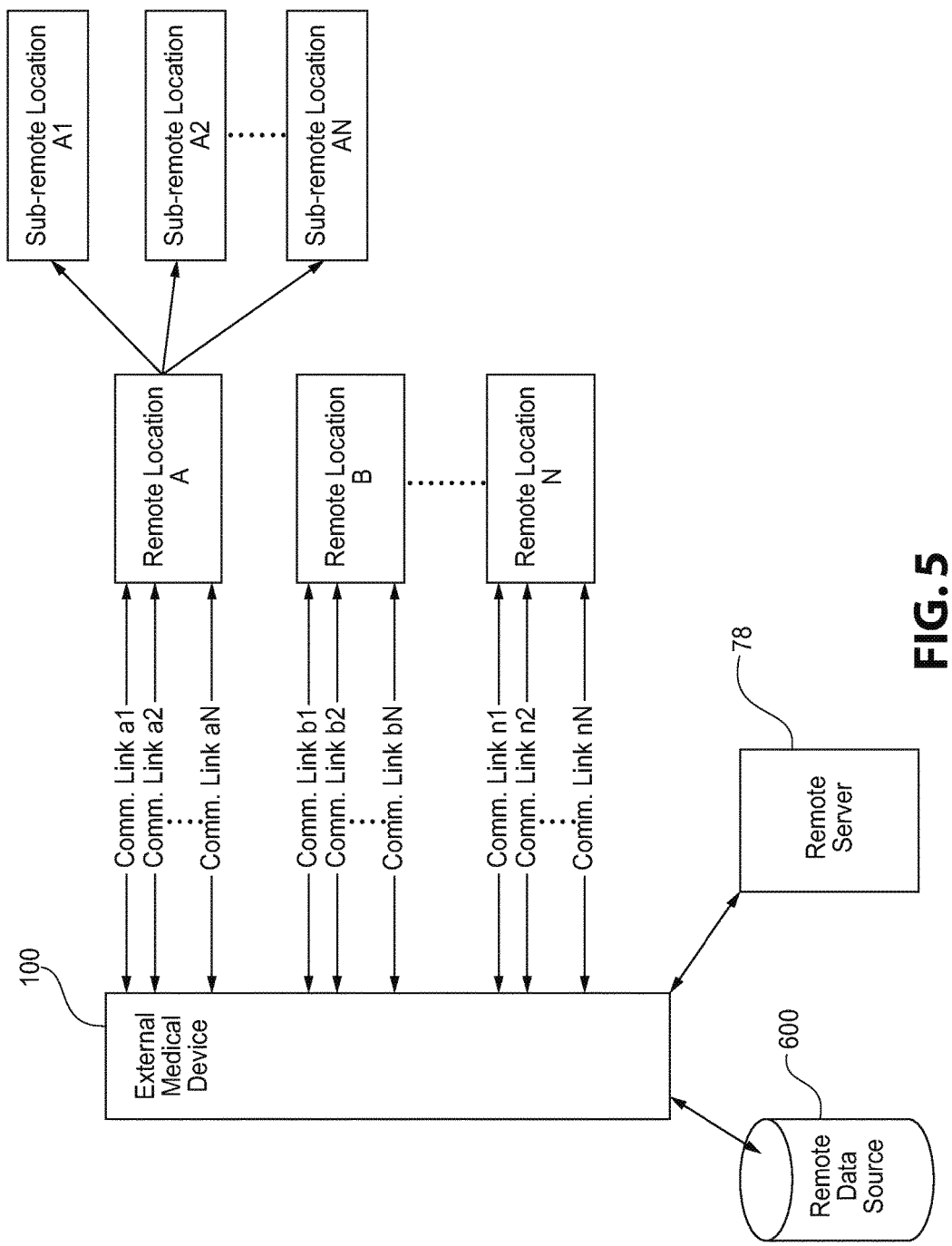
FIG. 5 is an example schematic diagram of a system for communicating data.
Figure 6:
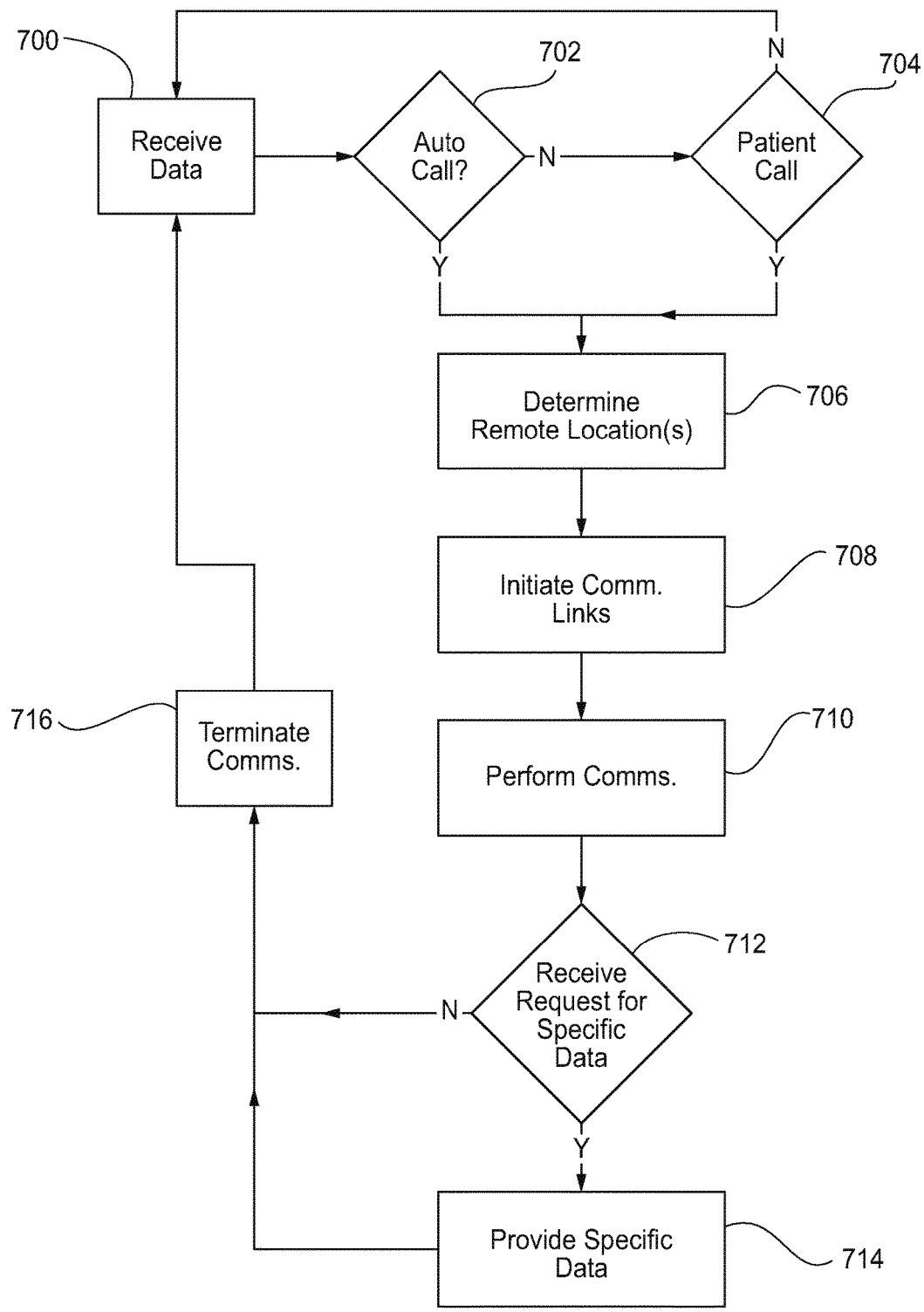
FIG. 6 is a flow chart illustrating operation of a system for communicating data.

In an example and with reference to FIGS. 5 and 6, the external medical device 100 receives data associated with the external medical device 100 and/or the patient 9 using the external medical device 100 at stage 700. The external medical device 100 can sense or collect the data and/or receive the data from one or more remote data sources. The remote data sources can include the remote server 78, remote locations A, B, . . . N, and/or another remote location, such as, a remote database 600 that stores patient data associated with patients that have been assigned external medical devices and/or device data associated with the external medical devices assigned to the patients.

The data received and/or sensed by the external medical device 100 can include physiological data of the patient 9 (e.g., ECG data from the electrodes 7a-7d and/or other data from other devices or sensors, such as, but not limited to, heart beat sensors, accelerometers, and sensors capable of measuring blood pressure, heart rate, glucose levels, blood oxygen levels, thoracic impedance, respiration rate, lung fluids, sleep data, heart and/or lung sounds, acoustics, audio, and/or the activity level of the subject), data indicating a change in a physiological condition of the patient 9, data indicating a stress level of the patient 9, patient symptoms (e.g., shortness of breath, light headedness, racing heart, skipped beat, fatigue, fainting, chest discomfort, and other symptoms, patient activity level (e.g., resting, light activity, moderate activity, and rigorous activity), demographic data of the patient (e.g., a name, medical history, insurance information, age, weight, sex, and/or other identifying information of the patient), a preference of the patient for a particular remote location (e.g., a patient selected hospital and/or a location associated with a patient selected doctor), operation data associated with an operation of the external medical device 100 (e.g., recent system activity and/or diagnostics, error codes, battery status, and/or communications status or availability), a location of the external medical device 100 (e.g., a GPS coordinates of the device), a location of the external medical device 100 with respect to the remote location (e.g., a distance of the device 100 from the remote location via GPS coordinates and/or a mapped route), a reason for initiating the communication link (e.g., a technical issue with the device 100, such as, an error code or patient requesting help regarding operation of the device 100, and/or a medical event of the patient), a language preference of the patient, a priority level of the communication link (e.g., a time from and/or severity of a prior medical event of the patient, a time from a prior treatment applied by the device 100, and/or a type of error code or malfunction), a treatment event of the external medical device 100 (e.g., a shock applied by the device 100 the patient and/or an attempted treatment canceled by the patient or aborted by the device 100), a detected cardiac event of the patient (e.g., a detected cardiac arrhythmia, such as, ventricular fibrillation or ventricular tachycardia), a type of the external medical device 100 (e.g., a model type and/or a software version), battery data on a battery of the external medical device 100 (e.g., battery level and/charging efficiency), a technical issue associated with the external medical device 100 (e.g., a specific error code and/or a specific malfunctioning component of the device 100), a representative who assigned the external medical device 100 to the patient, a caregiver associated with the patient (e.g., a doctor and/or a family member), and/or a type of insurance associated with the patient. With respect to sleep data, the device 100 may receive and/or sense information relating to sleep apnea, an indication of a time when the patient goes to sleep, and/or sleep data covering a period of time during which the patient is asleep such as ECG data, heart and lung sounds, respiration, etc.

Figure 7:
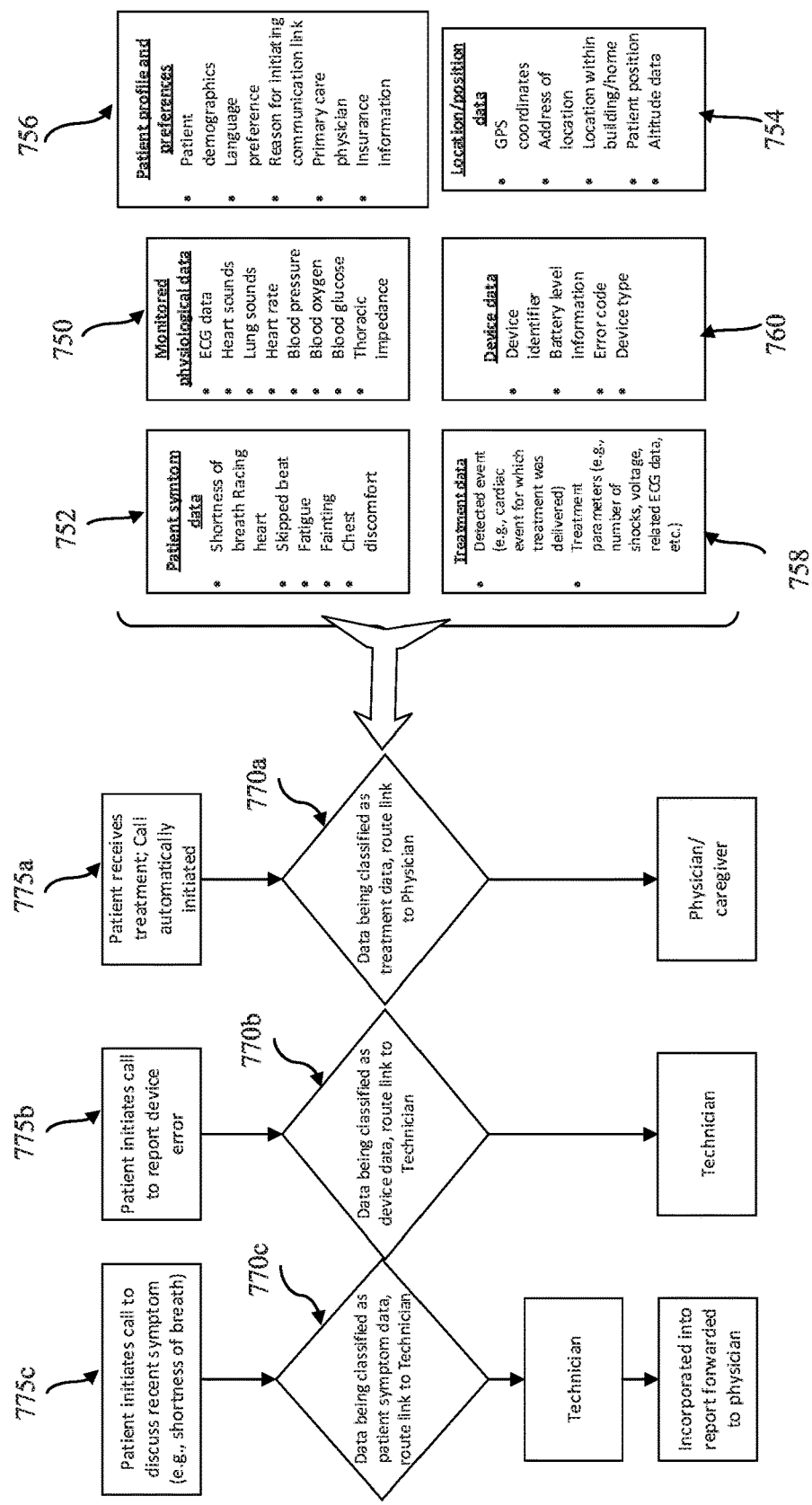
FIG. 7 is a flow chart illustrating classification or categorization of data.

In some examples, the data summarized above can be grouped into a plurality of categories and/or lists. For example, as shown in FIG. 7, such categories and/or lists can include monitored physiological data 750, patient symptom data 752, location/position data 754, patient profile and preferences data 756, treatment data 758, and device parameter data 760, among others. The device 100 can group the data into the plurality of categories and/or lists when the data is received, determined, or created, e.g., when the device 100 receives or senses the data, or in response to one or more actions or operations performed by the device 100 that result in the creation, modification, or use of the data. The device 100 can analyze the data to determine a category in which to classify the data based on the contents of the data itself, associations of the data with other data or operations of the device 100, and/or input from a user.

In some implementations, one or more categories can include subcategories and/or sublists for further classifying the data. In some implementations, the data and/or events can be preset such that they belong to default categories, lists, subcategories, or sublists, and may be modified by a user via a user interface. In some instances, a user (e.g., patient, patient service representative, or a caregiver) may add a new data/event item and accord it to one of an existing or a new user-defined category, list, subcategory, or sublist.

One or more of the above categories, lists, subcategories, and sublists can be associated with one or more remote locations (e.g., caregiver's location/office, service technician's location/office, or a patient's relative or loved one). In some implementations, one or more of the categories, lists, subcategories, and sublists may be associated with one or more actions to be taken on detecting data belonging to the categories, lists, subcategories, and/or sublists.

In an example, the device 100 can be configured to determine data associated with a communication link (e.g., by automatically collecting the data based on a detected patient or device event, or through patient input as described in detail below), determine a category (e.g., including subcategories) in which to classify the data based on one or more predetermined or user-defined categories, and select a remote location from a plurality of remote locations based on the determined category. For example, the device 100 can determine the category in which to classify the data based on user input as described in further detail below. For example, the device can determine the category in which to classify the data based on one or more characteristics of the data.

For instance, if the device 100 has recently encountered an error, and the user (e.g., patient 9) initiates a communication link, the device 100 may automatically collect information about the error code, and associated device error information and based on the characteristics of this data as being related to the device, classify the data as device data 760. The user then has the ability to confirm the purpose of the communication link as being related to the device data 760 and be routed to a technician to discuss the issue.

For example, as shown in FIG. 7, in scenario 770a, the device 100 can classify the data associated with the communication link as treatment data 758, in scenario 770b, the device 100 can classify the data associated with the communication link as device data 760, or in scenario 770c, the device 100 can classify the data associated with the communication link as patient symptom data 752. In some implementations, the device 100 can provide the data associated with the communication link to the selected remote location and/or initiate a communication link with the selected remote location based on the data category.

For example, the monitored physiological data category or list 750 can include information relating to a monitored physiological condition of the patient including data indicating an activity level of the patient, monitored ECG data, heart sounds, lung sounds, monitored tissue and/or lung fluids, blood pressure, heart rate, glucose levels, blood oxygen levels, thoracic impedance, respiration rate, sleep data, acoustics, data indicating stress levels of the patient 9, and data indicating a change in any of the monitored physiological conditions, among others. In some examples, the monitored physiological data category 750 can include one or more subcategories or sublists of heart-related data (e.g., ECG, heart sounds, etc.), activity related data (e.g., heart rate, activity level data, etc.), sleep-related data (e.g., time when patient goes to sleep, respiration or breathing data, etc.), among others.

For example, patient symptom data 752 can include shortness of breath, light headedness, racing heart, skipped beat, fatigue, fainting, chest discomfort, and other symptoms. For example, such patient symptom data may be recorded by a caregiver, the patient, or other user as appropriate in the circumstances.

For example, location/position data 754 can include details relating a patient's location including GPS coordinates, address of location, location within a building or a home, position (standing, laying down, etc.), and altitude from a reference level, among others.

For example, patient profile and preference data 756 can include one or more patient profile and preferences information including demographics information (age, gender, medical history, etc.), a language preference of the patient, a reason for selecting the communication link, data indicating a representative who assigned the patient the wearable medical device, a primary care physician or other caregiver assigned to the patient, insurance data, among others.

For example, treatment data 758 can include, in the context of a treatment device, information relating to a treatment event of a wearable medical device, including treatment for a detected cardiac event of the patient (e.g., a detected cardiac arrhythmia, such as ventricular fibrillation or ventricular tachycardia), and treatment parameters (e.g., number of shocks, voltage, related ECG data, etc.), among others.

For example, device parameter data 760 can include, among others, a battery level of a battery pack of the device, a unique device identifier, device type, device technical history (e.g., prior reported conditions, prior service information), and technical data associated with a reported technical issue of the device (e.g., a specific error code and/or a specific malfunctioning component of the device 100).

The external medical device 100 can receive, sense, and/or collect the data associated with the external medical device 100 and/or the patient 9 using the external medical device 100 in periodic or aperiodic time intervals or times, in dynamic time intervals or times, and/or in a continuous or substantially continuous manner. For example, the times during which the data collection occurs can be triggered by a user-initiated action and/or other event. For example, such times can be user configurable. In one example, the external medical device 100 can continuously or substantially continuously collect the data over a period of time during which the patient 9 is associated with the external medical device 100. Accordingly, the collected data may provide a timeline of data on the device 100, the patient 9, and/or the environment of the patient 9 during the time period. For example, the external medical device 100 can continuously or substantially continuously monitor the cardiac condition, e.g., an ECG signal, of the patient 9 during the period of time during which the patient is continuously or substantially continuously wearing or using the external medical device 100.

In another example, the external medical device 100 can receive, sense, and/or collect the data in response to a user instruction. For example, a caregiver may instruct the device 100 to record an ECG of the patient for a period of time or the patient 9 may instruct the device to begin recording the ECG, e.g., when the patient is experiencing a particular symptom.

For example, the patient can be provided with a drop down menu or check list that allows the patient to select a particular symptom from a list of options. Options for patient systems can include one or more of: feeling a skipped beat, shortness of breath, light headedness, racing heart rate, fatigue, fainting, chest discomfort, weakness, dizziness, and/or giddiness. Once the patient symptom is selected, the patient can identify his or her level of physical activity when the symptom was experienced. The patient can select a level of activity from a list including options, such as, resting, light activity, moderate activity, or rigorous activity. Once the activity level is selected, the user can initiate a data transmission from the device 100 to the remote server 78 and including relevant physiological information by, for example, selecting a "Submit" button.

In the context of a patient-initiated data transmission, for example, in response to the selection by the patient, the device 100 can capture a portion of the physiological signal for a period of time when the symptom was experienced (e.g., in the case of an ECG signal, such a portion can be in the form of an ECG strip). The device 100 can establish communication with the network, and send the captured portion of physiological information to the remote server 78. For example, a captured ECG stream can be a strip of about less than a minute. For example, a captured ECG strip that is associated with the symptom information can have a duration of approximately one minute. In some cases, the ECG strip can have a duration that is appropriate for the symptom(s) reported by the patient and/or event detected by the device 100. In some situations, it may be appropriate for the ECG strip recording to be of a duration lasting up to an hour (e.g., in the event of a recorded atrial flutter).

In some implementations, the patient monitor 20 can continuously record ECG data, and, at the same time, also record an ECG strip relating to one or more events of interest (e.g., patient-reported symptoms). As such, if a physician wishes to view ECG data for a period of time prior to or after the recorded ECG strip relating to an event of interest, such data is available for review from the continuously recorded ECG data stream.

Still referring to FIG. 7, in an example scenario 775a, if the device 100 automatically initiates a communication link in response to the patient 9 receiving a treatment from the device 100 (e.g., a treatment for a cardiac arrhythmia event), the device 100 can automatically detect and classify the information associated with the communication link as being related to the treatment. For example, the device 100 may detect and classify the data associated with the communication link as belonging to the treatment data category 758 based on the detected cardiac arrhythmia event and one or more treatment parameters, such as, a number of shocks, voltage, related ECG data, etc. Based on the communication link (e.g., classification of the data associated with the communication link as treatment data), the device 100 can select a remote location from a plurality of remote locations and initiate a communication link and/or provide the data to the selected remote location. For example, the data classified as treatment data 758 can be directly provided to a physician, caregiver, and/or other designated person.

In scenario 775b, if the patient 9 initiates a communication link to report a device error, e.g., a battery error, the device 100 can prompt the patient to input a reason for the communication link as described in further detail below. In some implementations, the device 100 can automatically detect the device error event (e.g., based on a device error code) and collect associated data relating to the event. Based on the communication link (e.g., either or both the patient's input and collected data associated with the communication link), the device 100 can then classify the data as belonging to the device data 760 category. For example, based on the classification of the data associated with the communication link as device data, the device can select a remote location from a plurality of remote locations and initiate a communication link and/or provide the data to the selected remote location. For example, the data classified as device data 760 can be provided to a technician location for analysis and troubleshooting the device error event.

In scenario 775c, if the patient 9 causes the device 100 to initiate a communication link to discuss a symptom, e.g., shortness of breath, the device 100 can classify this information as patient symptom data 752 and, based on the communication link (e.g., classification of data as patient symptom data 752), can select a remote location from a plurality of remote locations and initiate a communication link and/or provide the data to the selected remote location. In an implementation, the patient 9 can be provided with a screen before the link is initiated so that he or she can select the reason for the communication link as being a patient-reported symptom. In some instances, after the patient 9 reports the symptom or if the device 100 detects the symptom (e.g., based on the patient's respiration pattern), the communication link can be automatically initiated.

For example, the patient symptom data 752 relating to the shortness of breath can be provided to a technician location for reviewing or editing the data before providing the data in a report to a physician location. For example, the patient symptom data 752 can include an ECG strip or recording associated with the shortness of breath event. In some instances, the patient symptom data 752 can be directly sent to the physician or caregiver (or his or her designee). In some implementations, the device 100 can sent a notification directly to the physician or caregiver that a patient-initiated symptom has been recorded, and also send the patient symptom data 752 to a technician for generating a report to the physician or caregiver.

In some implementations, the patient 9 and/or user of device 100 can be afforded an opportunity to select one or more remote locations as destinations with which one or more communication links is to be established. For example, after a treatment is delivered in accordance with scenario 775a, the device 100 may prompt the patient 9 to select a remote location immediately after treatment is delivered. For example, in some instances, the patient 9 may opt call his physician's office. In other instances, the patient 9 may choose to place an emergency services call to an emergency services location (e.g., "911 call") directly from the device 100 to summon help from a rescue squad. In yet other situations, the patient 9 may opt to initiate a conference call including both his or her physician's office and a loved one.

In an implementation, the device 100 can initiate a communication link with the patient's relative (e.g., by dialing the relative's phone number). The device 100 can also automatically sent a notification message (e.g., text or audio) to the patient's physician notifying the physician about the treatment event and/r providing data relating to the treatment event.

In some implementations, prior to initiation, after initiation, or during a communication link, the device 100 can automatically receive, collect, and/or transmit (or the patient 9 can be prompted to provide) additional information needed for assisting the patient 9. For example, if the patient 9 (or technician) has initiated a communication link between the patient 9 and the technician to discuss a battery related error, and the technician wishes to learn about the last time the device carried out a self-test of the charging system, the device 100 can be configured to send this additional information. The device 100 can group the data for this additional information into the plurality of categories and/or lists based on the communication link and/or the data itself. For example, data for additional information related to the battery related error can be group into the device data category 760 and transmitted to the technician.

In an example, the external medical device 100 can automatically begin to receive, sense, and/or collect the data in response to a particular time and/or based on previously recorded data. For example, data indicating a technical issue or medical event that occurred at a particular time of day and/or with respect to a particular operation of the device 100 can cause the device 100 to automatically being to collect the data when that particular time of day and/or medical event occurs again. In some examples, the external medical device 100 can monitor some parameters of the patient 9 and/or the device 100 and, based on the monitored parameters, determine additional parameters of the patient 9 and the device 100 to begin monitoring.

In another example, the patient may be provided with one or more requirements for wearing or using the external medical device 100, e.g., that the device 100 must be worn for a certain duration during a particular time period and/or at specific times of the day or week. The external medical device 100 can monitor a compliance of the patient with the requirement for wearing or using the external medical device 100 during the time period and generate data indicating the compliance of the patient. The external medical device 100 can monitor a compliance of the patient with the requirement for performing one or more device related or guided activities (e.g., six-minute walk tests) and generate data indicating the compliance of the patient. Compliance data can be transmitted to one or more remote locations over one or more communication links. The patient and/or other user can discuss the compliance data with a caregiver or support person over the one or more communication links.

The external medical device 100 can monitor patient training and generate data relating to the training for use in the communication link (e.g., the patient and/or other user can discuss the details of the patient training with a caregiver or support person).

In an example and with continued reference to FIGS. 5 and 6, the external medical device 100 can, at stage 702, automatically initiate or begin a process to initiate a communication link with one or more of the remote locations A, B, . . . N based on the above-described data and/or analysis performed in connection with the external medical device 100 and/or the patient 9. The external medical device 100 may process the data, e.g., against one or more rules, and automatically initiate a communication link(s) with a remote location(s) if the data satisfies the one or more rules. For example, the external medical device 100 may automatically initiate a communication link with a medical professional, a hospital, and/or a close relative if a predetermined patient condition occurs, e.g., the ECG data of the patient indicates a possible cardiac arrhythmia. The device 100 may automatically initiate a communication link after the patient has responded to a possible arrhythmia condition by pressing the response button or after the patient has been treated.

Similarly, the device 100 may automatically initiate the communication link in response to detecting an incorrect assembly for the garment (e.g., detecting that one or more electrodes have been incorrectly inserted into one or more pockets of the garment). In another example, if the device 100 detects a device abuse event or indication, e.g., the device 100 suffers an impact exceeding a threshold amount, the device may automatically initiate the communication link. For example, the device 100 may include an Equipment Abuse Notification as described in U.S. Pat. No. 8,676,313 titled "Wearable medical treatment device with motion/position detection," which is hereby incorporated by reference in its entirety. If certain mechanical conditions that may lead to equipment damage such as mechanical shock or vibration are detected by accelerometers in the device 100 then device 100 can notify the user of such conditions and advise the user by the monitor computer screen. Similarly, if the monitor or belt is dropped or if they are hit with some other object causing a force greater than a predefined acceptable force, then the device 100 can provide either an audio or visual (display) indication to the patient that the event has occurred and warn against allowing such an event to occur again. If continuous vibration above a certain predefined acceptable threshold is detected for a period of time then the monitor may also provide a warning to the patient. Such vibration could lead to electrode or therapy pad fall-off or even cause false arrhythmia detection if enough physical motion is applied to the electrode and cables.

In addition, the device 100 may either automatically initiate or prompt the user with a screen indicating that the user, if he wishes, may initiate the communication link. In some examples, the device 100 can automatically record the device abuse information and transmit the information to a remote location via a communication link. For example, the communication link may not be immediately initiated following the device abuse event, but the device abuse information may be stored on a memory of the device 100 and communicated to a remote location at a later time during another communication link.

In some examples, the device 100 may apply one or more predictive algorithms to the measured physiological information to provide an estimation or prediction for occurrence of a potential medical event for a subject within an associated period of time. The estimation or prediction can be provided in the form of a risk score which can be based on, for example, physiological measurements extracted from the ECG signal including heart rate variability, PVC burden or counts, activity, noise quantifications, atrial fibrillation, momentary pauses, heart rate turbulence, QRS height, QRS width, changes in the size or shape of the morphology, cosine R-T, artificial pacing, corrected QT interval, QT variability, T wave width, T wave alternans, T-wave variability, ST segment changes, early repolarization, late potentials, fractionated QRS, or fractionated T wave content. The risk score can indicate, for example, that a patient's condition is generally improving, worsening, or remaining stable. Further, risk score values can be used to determine whether to automatically initiate the communication link or suggest to the patient and/or a bystander or a relative to call the patient's caregiver or an emergency response center.

In another example, the external medical device may automatically initiate a communication link with a technical support center if a particular error code or technical information relating the device 100 is received.

In another example, the external medical device 100 can initiate or begin a process to initiate a communication link with one or more of the remote locations A, B, . . . N in response to a user instruction at stage 704. As described herein with reference to FIG. 2, the user, e.g., the patient 9, caregiver, a patient service representative, a bystander, etc., can actuate a "call" button 53 to call one or more remote locations associated with the "call" button in the device 100.

Figure 8:
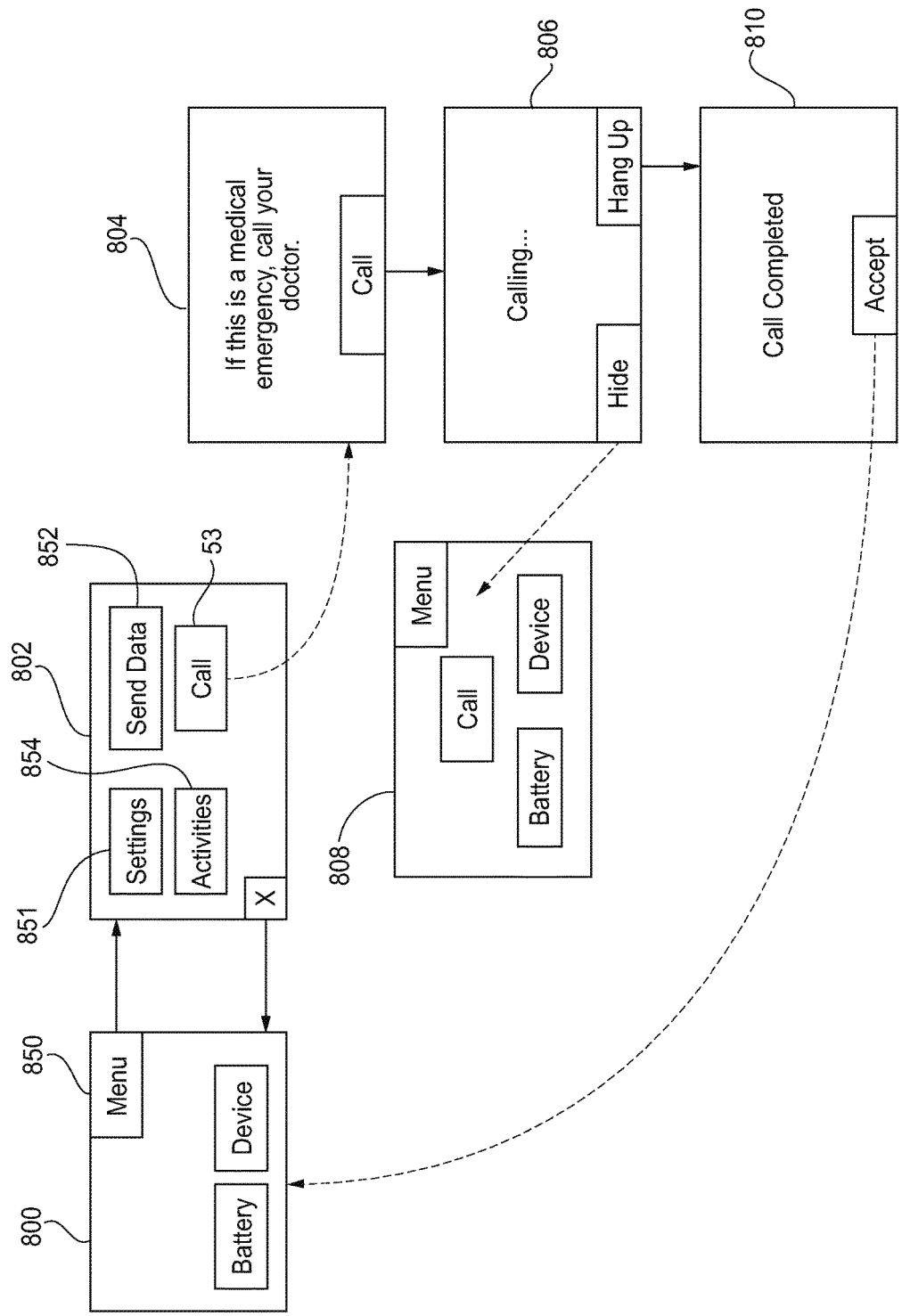
FIG. 8 illustrates an example user interface of a wearable medical device.

Referring to FIGS. 2 and 7, in some examples, the display screen 43 can display the "call" button 53 as an icon selectable by the patient 9 via the user interface provided by the display screen 43 and which places a call to a remote location associated with or assigned to the icon displayed by the display screen 43 in response to actuation of the icon. In stage 800, the user can select a menu icon 850 displayed in a main screen of the user interface to cause the user interface to display a menu of options for controlling the external medical device 100. The menu can include a settings icon 851 for opening a settings menu for setting and controlling settings of the external medical device 100, a send data icon 852 for controlling the external medical device 100 to transmit data to a remote location, an activities icon 854 for controlling the external medical device 100 to perform one or more operations, such as, execute a diagnostics program or monitor a particular type of data, and an icon for the "call" button 53. In stage 802, the patient 9 can select the "call" button 53 to indicate a desire to call the remote location associated with the icon, which, in the example shown in FIG. 8 is technical support.

In stage 804, the external medical device 100 can display a warning screen to ensure that the user is calling the correct remote location. For example, as shown in FIG. 8, the warning screen can require the patient 9 to again actuate an icon for the "call" button 53 while providing a warning that the patient 9 should call a doctor if the patient 9 is experiencing a medical emergency. If the patient 9 actuates the icon for the "call" button 53, in stage 806 the external medical device 100 initiates the call and displays a call screen indicating that the call has been initiated and providing an icon selectable by the user to "hide" the call screen and instead display the main screen (stage 808) and an icon to end the call. Otherwise, the external medical device 100 can return to the menu screen and await further instruction from the user. After the call has been completed, the external medical device 100 can display a call completed screen in stage 810 that indicates the call has been completed and provides the user with an icon to return the user interface to the main screen.

In an example and referring again to FIGS. 5 and 6, the external medical device 100 can determine or select one or more of the remote locations A, B, . . . N with which to initiate one or more communication links a1, a2, . . . aN . . . n1, n2, nN based on the data associated with the external medical device 100 and/or the patient 9 using the external medical device 100 at stage 706. For example, the external medical device 100 may determine a telephone number to call or other communications address associated with a remote location and initiate the call by executing the protocols required to establish the communication link. In another example, the external medical device 100 can initiate the call, and the call can be routed to the selected remote location based on the data associated with the external medical device 100 and/or the patient 9 using the external medical device 100.

The external medical device 100 can apply a plurality of rules to the data associated with the external medical device 100 and/or the patient 9 using the external medical device 100 to determine or select the one or more remote locations A, B, . . . N with which to initiate a communication link. The external medical device 100 can initiate a single communication link, e.g., a1, with a remote location, e.g., A, and communicate different types and/or amounts of data over the single communication link, or the external medical device 100 can initiate multiple communication links, e.g., a1, a2, . . . aN, with a single remote location, e.g., A, and communicate different types and/or amounts of data over the different communication links. The external medical device 100 can determine a number of communication links to initiate with a remote location based on a type and an amount of data that required or requested to be sent to the remote location.

In some examples, a first remote location A can be a remote location for providing technical support for the external medical device 100 and a second remote location B can be associated with a caregiver of the patient. In some examples, a third remote location C can be associated with emergency response services, e.g., a 911 services or rescue squad.

The external medical device 100 can select one of the first remote location A and the second remote location B based on data associated with an operation of the external medical device 100. For example, if the device 100 generates an error code, the first remote location A for providing the technical support can be selected, and if the device determines that the patient 9 is experiencing or has recently experience a medical event, the second remote location B associated with the caregiver of the patient can be selected.

In other examples, the external medical device can select each of the first remote location A and the second remote location B based on the data associated with an operation of the external medical device 100 and initiate a communication link with each of the first remote location A and the second remote location B. The communication link with the first remote location A can be separate and independent from the communication link with the second remote location B. Alternatively, a single communication link that incorporates communications between the device 100, the first remote location A, and the second remote location B can be initiated by the device 100. For example, the device 100 can initiate a conference call between the patient 9, a doctor, and a relative of the patient 9, or between the patient 9, technical support, and a caregiver of the patient 9.

In some examples, the patient or other user may be in need of training on or assistance with one or more aspects of the medical device 100. As such, the patient may initiate the communication link (e.g., by pressing the "call" button or other such action) to request live support or one or more training modules relating to the one or more aspects of the device 100. For instance, if the patient is need of training on how to assemble the garment associated with the device 100, he may initiate a communication link to request the information. In some implementations, one or more patient service representatives may request, through the use of the "call" button, for assistance with garment fitting on the patient.

Alternatively, the device 100 may automatically initiate the communication link in response to detecting an incorrect assembly for the garment (e.g., detecting that one or more electrodes have been incorrectly inserted into one or more pockets of the garment). Similarly, if the device 100 detects a device abuse indication, e.g., the device 100 suffers an impact exceeding a threshold amount, the device may automatically initiate the communication link.

Once the link has been established, the device 100 can relay to the remote location supporting data relating to the event that triggered the automatic call which may then be reviewed at the remote location (e.g., technical support) and discussed with the user. Further, the device may be configured to automatically download a relevant training module and the user may either maintain the link for the duration of the training or end the communication and execute the training module. For example, the training module may be configured for independent patient and/or user learning without a need for any other person's assistance.

In some implementations, a remote location may initiate a communication link to the device 100 for a number of reasons. For example, if a patient 9 has recently received treatment, the physician's office may receive notification of the treatment event. The physician or his or her designee may contact the patient 9 directly via the device 100 to communicate with the patient 9. Similarly, if a device event is noted (e.g., a device error code, or battery level is dangerously low), a technician may initiate a communication link to the device 100, e.g., an audio call to speak to the patient 9. In various implementations, the remote location and/or the patient 9 may communicate via textual messages as provided in further detail below.

In another example, the external medical device 100 can determine or select one or more of the remote locations A, B, . . . N with which to initiate a communication link(s) based on data associated with a plurality of different possible remote locations. The data associated with the plurality of possible remote locations can include a type of the remote location (e.g., technical support, medical support, software support, etc.), a schedule of availability of the plurality of possible remote locations (e.g., operating hours, personnel availability, etc.), a location of the plurality of possible remote locations, and a type of personnel assigned to the plurality of possible remote locations (e.g., doctor specialty, technical support specialty, etc.).

The external medical device 100 can receive the data associated with the plurality of possible remote locations directly from the remote locations A, B, . . . N themselves, from the remote server 78, and/or from the remote data sources 600. The external medical device can apply a plurality of rules to the data associated with the plurality of possible remote locations and the data associated with at least one of the external medical device and the patient using the external medical device 100 to select one or more of the remote location A, B, . . . N from the plurality of possible remote locations with which to initiate a communication link(s). For example, a remote location may notify the external medical device 100 that it is no longer suitable for to contact at a particular time or with respect to a particular technical issue or medical event, e.g., a remote location schedule is full or a particular type of doctor or technical support agent is not available at the remote location, and the electronic medical device 100 can select a different one or more of a the remote locations A, B, . . . N based on this data.

In an example, the external medical device 100 can determine or select one or more of remote locations with which to initiate a communication link based on a previous communication link initiated by the device 100 with a previous remote location. The remote location can be determined or selected based on a plurality of different previous communication links initiated by the device 100 with a plurality of different previous remote locations, e.g., data similar to a call history log. For example, the remote location can be selected based on a particular technical support agent or doctor associated with the previous remote location.

For example, a history of a plurality of previous communication links as used herein can include details regarding a time when the link was initiated, an indication of the reason for the link (e.g., a technical question, a device error, a health related question, a training request, or any other question), and/or any device or patient information recorded in association with the communication link. For example, a log may be stored on the device 100 with all of or a portion of the available information associated with the plurality of communication links. In some examples, a log may be stored at one or more remote locations and made available to the device via a secure communication link as needed.

In another example, the external medical device 100 can determine or select one or more of remote locations with which to initiate a communication link based supporting data transmitted by the device 100 to the previous remote location. For example, if technical information about the device 100 is to be sent to a remote location with which a communication link is to be initiated by the external medical device 100, the device 100 can determine based on the technical information that the communication link should be initiated with a particular technical support location based on the technical information about the device 100 if the same or similar type of information was previously transmitted to the particular location.

With continued reference to FIGS. 5 and 6, the external medical device 100 initiates a communication link(s) with the selected remote location(s) at stage 708. In an example and as shown in FIG. 5, the external medical device 100 can initiate one or more of communication links a1, a2, . . . aN with remote location A, one or more of communication links b1, b2, . . . bN with remote location B, and/or one or more of communication links n1, n2, . . . nN with remote location N. A communication link can comprise an audio and/or video communication link capable of communicating audio and/or video data between the external medical device 100 and a remote locations. The audio and/or video data may comprise live or real-time audio and/or video. For example, an audio and/or video communication link may comprise a real-time telephone call, a real-time video call (e.g., a Skype® call, a FaceTime® call, or other video conferencing call), a Push-to-Talk (PTT) connection, or other communication link capable of communicating audio and/or video data between two parties. In another example, one or more of the communication links, e.g., a1, a2, . . . aN, between the external medical device 100 and a remote location, e.g., A, may comprise a communication link that need not be an audio and/or video communication link. For example, one or more of the communication links may comprise a data communication between the external medical device 100 a remote location for the purpose of transmitting and/or receiving any type of data, e.g., the data associated with the external medical device 100 and/or the patient 9 using the external medical device 100.

In an example, after initiating a first communication link with a selected first remote location, the external medical device 100 can automatically, or in response to a user's request, initiate a second communication link, e.g., b1, with the selected first remote location or a predetermined second remote location. In this manner, the device 100 may be configured to maintain one or more concurrent or substantially concurrent communication links with a plurality of remote locations.

The external medical device 100 can select a first remote location, e.g., remote location A, with which to initiate a communication link based on the data associated with the external medical device 100 and/or the patient 9 using the external medical device 100. The remote location A may be associated with a second remote location, e.g., remote location B, in the external medical device 100 such that the external medical device 100 automatically initiates a second communication link, e.g., b1, with the second remote location B whenever the first communication link a1 is initiated with the first remote location A. For example, the external medical device 100 can automatically call the phone number of a relative or loved one simultaneously or substantially simultaneously with or in response to initiating a call with a medical professional or technical support. In this manner, the relative or loved one is immediately notified when a medical event occurs, or the patient 9 is requesting help with the device 100. In some examples, the relative or loved one can be conferenced directly into the call between the external medical device 100 and the medical professional or technical support.

With continued reference to FIGS. 5 and 6, the external medical device 100 performs communications with the selected remote location(s) over the established communication link(s) at stage 710. For example, audio and/or video data can be communicated over an audio and/or video communication link between the external medical device 100 and a remote location, and supporting data can be communicated over the same or another communication link or channel between the external medical device 100 and the remote location. For example, if the remote location is a technical support agent, the patient 9 can communicate via audio, interactive two-way text messages, and/or video with the agent, e.g., explain a problem or issue with the device and/or receive instructions for addressing the problem and/or issue. Supporting data, including technical information about the device 100, can be communicated to the agent to assist the agent in providing technical support to the patient 9 using the device 100. If the remote location is a doctor, the patient 9 can communicate via audio, interactive two-way text messages, and/or video with the doctor, e.g., identify any symptoms or how they are feeling or receive instructions on how to react to a medical event. Supporting data in this scenario, including patient or device data, e.g., an ECG signal of the patient, can be communicated to the doctor to assist the doctor in providing medical support to the patient 9 using the device 100.

In an example, the external medical device can be operable to record the data associated with the external medical device 100 and/or the patient 9 using the external medical device 100 for a predetermined time period in response to a user instruction and automatically communicate the recorded data to a predetermined remote location. For example, in a hospital-based device as described herein, a nurse can instruct the device to record an ECG signal of the patient over a period of time and automatically upload the ECG recording to a remote location for analysis. In some examples, an identifier of the user providing the instruction to record the data can be associated and transmitted with the data to the remote location. For example, the nurse can be required to log on or satisfy an authentication procedure, e.g., a username and password, before providing instructions to the device 100, and the identifier of the nurse can be associated with operations of the device and data recorded and/or received by the device a during a time period in which the nurse is logged into the device as an authorized user. The nurse can set particular settings in the device to correspond to the patient 9 currently assigned to the device, e.g., different thresholds for automatic calls and/or alerts generated by the device 100 can be set for different users.

In an example, the external medical device 100 can provide supporting data to a remote location as noted above. The supporting data can include the data associated with the external medical device 100 and/or the patient 9 using the external medical device 100. For example, as noted above, the supporting data can include any of, without limitation, communication link-related data (e.g., an indication of a reason for the link), patient's insurance information, compliance data, any device abuse information, patient training data, monitored physiological information (cardiac and non-cardiac data), and/or any other device or patient information.

The external medical device 100 can provide the supporting data before initiating a communication link with the remote location, after initiating the communication link with the remote location, contemporaneously or substantially contemporaneously with initiating and/or maintaining communication via the communication link with the remote location, and/or after terminating the communication link with the remote location. For example, the external medical device 100 can send error codes or other technical information on the device 100 to a remote location providing technical support before or during initiation of a call with technical support so that technical support agent has data helpful in providing technical support for the device to the patient via the call. In another example, the external medical device may send patient data, e.g., ECG signals, to a remote location, such as, a doctor or a hospital, before, during, or after a call to the doctor or hospital in response to a medical event occurring with the patient 9 so that the doctor or hospital has data helpful in analyzing the medical event and/or the patient 9.

The external medical device 100 can provide the supporting data to the remote location via a same communication link that is used for audio, video, and/or other communications with the remote location or a separate link. In an example, the communication link can be routed to the remote location based on the supporting data. For example, the supporting data may include data including instructions for one or more remote systems or devices to route the call to a particular remote location.

In another example, the patient 9 (or other user initiating a call) may be prompted by the external medical device 100 to consent to the transmission and release of the supporting data to the remote location before the data can be transmitted to the remote location. The external medical device can provide a prompt to a user at least one of prior to initiating the audio and/or video communication link and prior to transmitting data to the remote location over the audio and/or video communication link. The user prompt can comprise a prompt for user consent to release information to the remote location. For example, the external medical device 100 can display a screen requesting that the patient 9 confirm the transmission and release of the supporting data by actuating a button on the device 100 or an icon representing a button in the user interface provided by the display.

The data communicated over the communication links, the supporting data transmitted to the remote location from the external medical device 100, and any other data provided from or received by the external medical device 100 can be protected by various encryption standards. For example, encryption standards that meet Health Insurance Portability and Accountability Act (HIPAA) compliance guides may be applied to data transmitted from and received by the external medical device 10, such as, using multi-factor authentication for encryption solutions and using the Advanced Encryption Standard (AES) for encryption algorithms, and centrally managing all storage encryption.

In another example and with reference to FIG. 5, the external medical device 100 can initiate a communication link with a remote location, and the communication link can be routed to a sub-location of the remote location based on supporting data provided to the remote location. As discussed herein, the external medical device 100 can provide the supporting data before or contemporaneously with initiating a communication link with the remote location via the communication link itself or another communication link. The remote location, e.g., remote location A, can use the supporting data to determine if the communication link should be routed to one or more of sub-locations A1, A2, . . . AN. For example, if the external medical device 100 initiates a communication link with a technical support location and transmits supporting data indicating that the device has experienced a particular type of software error, the technical support location can route the communication link to a sub-location suitable for addressing the particular type of software error based on the supporting data, and forward the supporting data to the sub-location.

In an example and with continued reference to FIGS. 5 and 6, the external medical device 100 can receive a request for certain data from one or more of the remote locations A, B, . . . N at stage 712. The external medical device 100 can provide the requested data to the requesting remote location in response to the request at stage 714. The external medical device 100 can transmit the requested data to the remote location over an existing communication link or initiate a new communication link for transmitting the requested data. For example, the external medical device 100 can have an already established audio and/or video communication link a1 with a remote location A, such as, a technical support center, and, in response to the request for data, initiate another communication link a2 with the remote location A over which the requested data can be transmitted, such as, device diagnostics data, error codes, etc.

In another example, at stage 714, the external medical device 100 can provide a remote location with direct access to certain data stored in a memory of the external medical device 100. For example, the external medical device 100 can provide direct access to device or patient data stored on the external medical device 100 such that the remote location can browse the data on the device 100 and download selected data from the device 100.

At stage 716, the external medical device 100 can terminate the communication link with the remote location and processing returns to stage 700. Although FIG. 8 shows that the external medical device 100 receives the data at stage 700, the external medical device 100 can receive the data throughout the entire process disclosed in FIG. 6. In some examples, the external medical device can update communication links, open new communication links with existing or new remote locations, and/or communicate updated or modified data based on new data associated with the external medical device 100 and/or the patient 9 using the external medical device 100 received during communication over a current communication link.

In one example, devices described herein can be capable of providing patient training or assistance. After leaving a doctor's office or a hospital, a patient 9 that has been assigned a device 100 may be unsure how to perform one or more operations associated with the device 100, e.g., changing batteries, applying electrodes, etc.

Figures 9A, 9B:
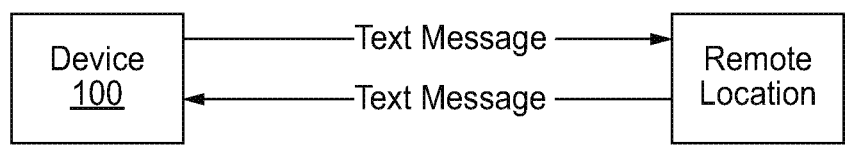
FIG. 9A illustrates another example user interface of a wearable medical device.
FIG. 9B is an example schematic diagram of a system for interactive communications.

Referring to FIG. 9A, before the device 100 initiates a communication link, e.g., before placing a call or initiating an interactive two-way text messaging session, the patient 9 can be prompted to indicate a nature of and/or a preferred remote location for the communication. In this manner, in some implementations as described above, the patient's input can be used as a basis for classifying a category of the data associated with the communication link. For example, the device 100 can provide the patient 9 with a series of options via the user interface that enables the patient 9 to indicate the nature of the communication, e.g., a technical question option, a device error code option, a health related issue option, a training request option, a report a device issue option, an "other" option, etc. In some implementations, the device 100 may also present the patient 9 with a series of options that enable the patient 9 to indicate a preferred remote location for the communication link. For instance, if the patient has reported a heath related issue, and selects to report a symptom, the patient may be afforded the opportunity to select to initiate a communication link with a caregiver to discuss the symptom, or a technician to provide more information relating to the symptom so that the information can be compiled into a report. The device 100 receives a selection from the patient 9 of an option via the user interface, and determines the remote location based on the option selected by the patient 9. The communication link can be routed to the remote location based on the option selected by the patient 9.

In another example, and referring to FIG. 9B, the device 100 can provide a text/image based interactive communication between the patient 9 and a remote location, (e.g., via text message, such as SMS message or MMS message, a real-time chat service, or other live support software that provides interactive communication between the patient 9 and a remote location), before, during, after, or in place of initiating an audio and/or video communication link with the remote location. For example, at stage 906, the device 100 can transmit a message including supporting information and/or the data received and/or sensed by the external medical device 100 to the remote location, e.g., to a technical support location or a location of a doctor for the patient 9. At stage 908, the messages can be routed based on the data received and/or sensed by the external medical device 100, information included in the messages by the device 100 or the patient 9, a nature of the message or a remote location selected by the user in response to a prompt from the device 100, or a remote location preset in the device 100. A communication link can be routed to a remote location based on the information in the messages exchanged in the interactive communication between the patient 9 and the remote location. In one example, the device 100 can prompt the user to indicate in a message to be transmitted the nature of the communication, e.g., a technical question option, a device error code option, a health related issue option, a training request option, a report a device issue option, and an "other" option, and the message or another communication link can be initiated and routed to the appropriate remote location based on the indicated nature.

In an example, a remote location can initiate an interactive communication with the patient 9 via the device 100, for example, by transmitting a message to the device 100. For example, a doctor for the patient 9 may transmit a message asking the patient 9 if they took a prescribed medication on schedule, requesting the patient to perform an activity while using the device 100 and send the monitoring results to the location of the doctor, or to follow-up on a device or patient related issue.

In another example, the device 100 can automatically trigger a message to be transmitted or a communication link to be initiated to the patient 9 from a remote location based on the data associated with the external medical device 100 and/or the patient 9. For example, the device 100 can trigger the message or communication link from the remote location in response to a determination of patient non-compliance with one or more operations or activities associated with the device 100 or the patient condition, e.g., not switching the battery, incorrect application or positioning of electrodes, or the patient 9 not wearing or using the device 100 in a prescribed manner, a device error code, a cardiac event detected for the patient 9, a detected pattern of the patient 9 performing an operation incorrectly, such as, holding a response button when a response is not required, detected abuse of the device, such as, an impact threshold of an impact sensor in the device 100 being triggered, and/or various device performance issues, such as, slow downloads, a pattern of device restarts or reboots, etc. The device 100 can select the remote location from which to trigger the message based on the data associated with the external medical device 100 and/or the patient 9. For example, a battery issue can trigger a message from a technical support location, while a cardiac event can trigger a message from a location associated with a doctor or hospital. In one example, the device 100 can prompt the patient 9 to indicate whether he or she needs to speak with someone before triggering the message or the communication link from the remote location.

For example, the patient 9 may need training on one or more aspects of the device 100 if the patient 9 does not comply with device instructions or the patient does not perform one or more requested or required actions. A remote location, such as, a technical support location, can send a message to the device 100 for the patient 9 that includes options for scheduling a call between the patient 9 and technical support. The patient 9 can respond with a message or selection that that indicates a time to schedule the call, an alternative phone number at which the patient 9 wants to receive the call, and/or other information associated with the device or patient condition. If a more urgent issue exists, e.g., the patient 9 received a shock from the device 100 or the device 100 predicts that the patient is at a high risk for cardiac event in a future time period, the remote location can transmit a message to the patient requesting that the patient 9 immediately contact the remote location, or the patient 9 can be automatically contacted by the remote location via the device 100.

The embodiments have been described with reference to various examples. Modifications and alterations will occur to others upon reading and understanding the foregoing examples. Accordingly, the foregoing examples are not to be construed as limiting the disclosure.

What is claimed is:

1. A wearable medical device configured to communicate with a remote location, the wearable medical device comprising:
    monitoring circuitry configured to monitor a cardiac condition of a patient using the wearable medical device; and
    communication circuitry configured to:
        provide a prompt to the patient that requests the patient indicate a nature of a communication,
        determine a category of data associated with a communication link from a set of data categories based on the patient indicated nature of the communication,
        select the remote location from a plurality of remote locations based on the determined category of the data, and
        initiate the communication link to the remote location based on the determined category of the data.

2. The wearable medical device of claim 1, wherein the plurality of remote locations comprise an emergency response location, a technician location, a physician location, and a relative or caregiver location.

3. The wearable medical device of claim 2, wherein the communication circuitry is configured to determine the category of the data as one of monitored physiological data, patient symptom data, location/position data, patient profile and preferences data, treatment data, and device parameter data.

4. The wearable medical device of claim 3, wherein if the determined category is patient symptom data, the communication circuitry is configured to provide the data to the technician location for reviewing or editing the data before providing the data to the physician location.

5. The wearable medical device of claim 3, wherein if the determined category is device data, the communication circuitry is configured to provide the data to the technician location.

6. The wearable medical device of claim 5, wherein the data is associated with an error code, wherein the error code is associated with a device error of the device, and wherein the communication circuitry is configured to determine the data based on the patient indicated nature of the communication.

7. The wearable medical device of claim 3, wherein if the determined category is treatment data, the communication circuitry is configured to provide the data to the relative or caregiver location.

8. The wearable medical device of claim 1, wherein the communication circuitry is configured to at least one of provide the data to the remote location via the communication link and initiate an audio and/or video communication link with the remote location.

9. The wearable medical device of claim 1, wherein the data is associated with the cardiac condition of the patient using the wearable medical device monitored by the monitoring circuitry, and wherein the communication circuitry is configured to
    provide options to a user for selecting a current symptom of the patient,
    receive a selection of the current symptom of the patient, and
    transmit the data in association with the current symptom of the patient to the remote location via the communication link.

10. The wearable medical device of claim 9, wherein the communication circuitry is configured to provide options to the user for selecting a level of physical activity of the patient associated with the current symptom, receive a selection of the level of physical activity, and transmit the data in association with the level of physical activity to the remote location via the communication link.

11. The wearable medical device of claim 1, wherein the communication circuitry is configured to provide the prompt to the patient based on the patient receiving a treatment from the device.

12. The wearable medical device of claim 1, wherein the prompt comprises a message to be transmitted including the request that the patient indicate the nature of the communication, and wherein the communication circuitry is configured to determine the category of the data based on the nature of the communication indicated in the message to be transmitted and transmit the message via the communication link.

13. A wearable medical device comprising:
    monitoring circuitry configured to monitor a cardiac condition of a patient using the wearable medical device; and
    communication circuitry configured to initiate an audio and/or video communication link with a remote location,
    wherein the communication circuitry is configured to provide a user with an option to control the communication circuitry to initiate the audio and/or video communication link with the remote location based on an operation associated with the wearable medical device, and wherein the device is configured to detect a pattern of the user performing an incorrect device operation and provide the user with the option to control the communication circuitry to initiate the audio and/or video communication link with a technician location based on the detected pattern of incorrect device operation.

14. The wearable medical device of claim 13, wherein the communication circuitry is configured to control a user interface of the wearable medical device to provide the user with the option to control the communication circuitry to initiate the audio and/or video communication link via user input to the user interface.

15. The wearable medical device of claim 14, wherein the communication circuitry is configured to control the user interface to display the option on a display screen as an icon selectable by the user via the user interface.

16. The wearable medical device of claim 13, wherein the operation associated with the wearable medical device includes at least one of: a system activity of the device, an error encountered by the device, a battery status of the device, a communications status or availability of the device, a user operation of the device, a performance of the device, or any combination thereof.

17. The wearable medical device of claim 13, wherein the incorrect device operation includes incorrect user input to a user interface of the device.

18. The wearable medical device of claim 13, wherein the wearable medical device comprises a wearable defibrillator.

19. A wearable medical device comprising:
monitoring circuitry configured to monitor a cardiac condition of a patient using the wearable medical device; and communication circuitry configured to initiate an audio and/or video communication link with a remote location, wherein the communication circuitry is configured to provide a user with an option to control the communication circuitry to initiate the audio and/or video communication link with the remote location based on an operation associated with the wearable medical device, and wherein the communication circuitry is configured to detect a pattern of device restarts or reboots and provide the user with the option to control the communication circuitry to initiate the audio and/or video communication link with a technician location based on the detected pattern of device restarts or reboots.

20. The wearable medical device of claim 19, wherein the wearable medical device comprises a wearable defibrillator.

* * * * *